(12) United States Patent
Kane et al.

(10) Patent No.: US 10,471,265 B2
(45) Date of Patent: Nov. 12, 2019

(54) IMPLANTABLE ANCHOR LOCKING MECHANISM

(71) Applicant: Nuvectra Corporation, Plano, TX (US)

(72) Inventors: Larry Kane, Roseville, MN (US); Elliot Bridgeman, Big Lake, MN (US)

(73) Assignee: NUVECTRA CORPORATION, Plano, TX (US)

( * ) Notice: Subject to any disclaimer, the term of this patent is extended or adjusted under 35 U.S.C. 154(b) by 7 days.

(21) Appl. No.: 15/728,997

(22) Filed: Oct. 10, 2017

(65) Prior Publication Data

US 2018/0099147 A1 Apr. 12, 2018

Related U.S. Application Data

(60) Provisional application No. 62/406,463, filed on Oct. 11, 2016.

(51) Int. Cl.
| | |
|---|---|
| *A61N 1/375* | (2006.01) |
| *A61N 1/05* | (2006.01) |
| *A61N 1/36* | (2006.01) |
| *A61M 25/04* | (2006.01) |

(52) U.S. Cl.
CPC ....... *A61N 1/37518* (2017.08); *A61N 1/0558* (2013.01); *A61M 25/04* (2013.01); *A61N 1/36062* (2017.08); *A61N 2001/0582* (2013.01)

(58) Field of Classification Search
CPC .............. A61N 1/37518; A61N 1/0558; A61N 2001/0582; A61N 1/36062; A61M 25/04
See application file for complete search history.

(56) References Cited

U.S. PATENT DOCUMENTS

| | | | |
|---|---|---|---|
| 7,787,960 B2 | 8/2010 | Lubenow et al. | |
| 8,140,172 B1 * | 3/2012 | Jones | A61M 5/14276 600/375 |
| 8,271,096 B2 * | 9/2012 | Rivard | A61N 1/057 606/232 |
| 8,301,268 B1 * | 10/2012 | Jones | A61N 1/0558 607/126 |
| 8,467,883 B2 | 6/2013 | Chen et al. | |
| 8,494,652 B2 | 7/2013 | Cantlon et al. | |
| 8,954,165 B2 * | 2/2015 | Sharma | A61N 1/0558 607/117 |
| 9,180,291 B2 * | 11/2015 | Leven | A61N 1/0558 |

(Continued)

*Primary Examiner* — Catherine M Voorhees
(74) *Attorney, Agent, or Firm* — Haynes and Boone, LLP; Eric Li

(57) ABSTRACT

A anchor for an implantable medical device includes an anchor body and a locking member. The anchor body includes a first trough extending along a first axis. The locking member is coupled to the anchor body and rotates with respect to a second axis, between an unlocked position and a locked position. The locking member includes protruding members that define a second trough aligned with the first trough when the locking member is rotated to the unlocked position, so as to form an open path for the implantable medical device to move through the first and second troughs. When the locking member is rotated to the locked position, the protruding members block at least a portion of the first trough to define a tortuous path between the first trough and the second trough so as to restrict a movement of the implantable medical device through the first and second troughs.

58 Claims, 24 Drawing Sheets

(56) References Cited

U.S. PATENT DOCUMENTS

| | | | |
|---|---|---|---|
| 9,198,649 B2* | 12/2015 | Karapetian | A61B 17/0401 |
| 2008/0196939 A1* | 8/2008 | Lubenow | A61N 1/056 |
| | | | 174/652 |
| 2009/0171156 A1* | 7/2009 | Yamaya | A61B 1/00082 |
| | | | 600/116 |
| 2012/0035692 A1* | 2/2012 | Cantlon | A61N 1/0558 |
| | | | 607/116 |
| 2012/0197367 A1* | 8/2012 | Olson | A61N 1/0558 |
| | | | 607/116 |
| 2015/0012076 A1 | 1/2015 | Jones | |
| 2015/0018914 A1* | 1/2015 | Leven | A61N 1/0553 |
| | | | 607/116 |

* cited by examiner

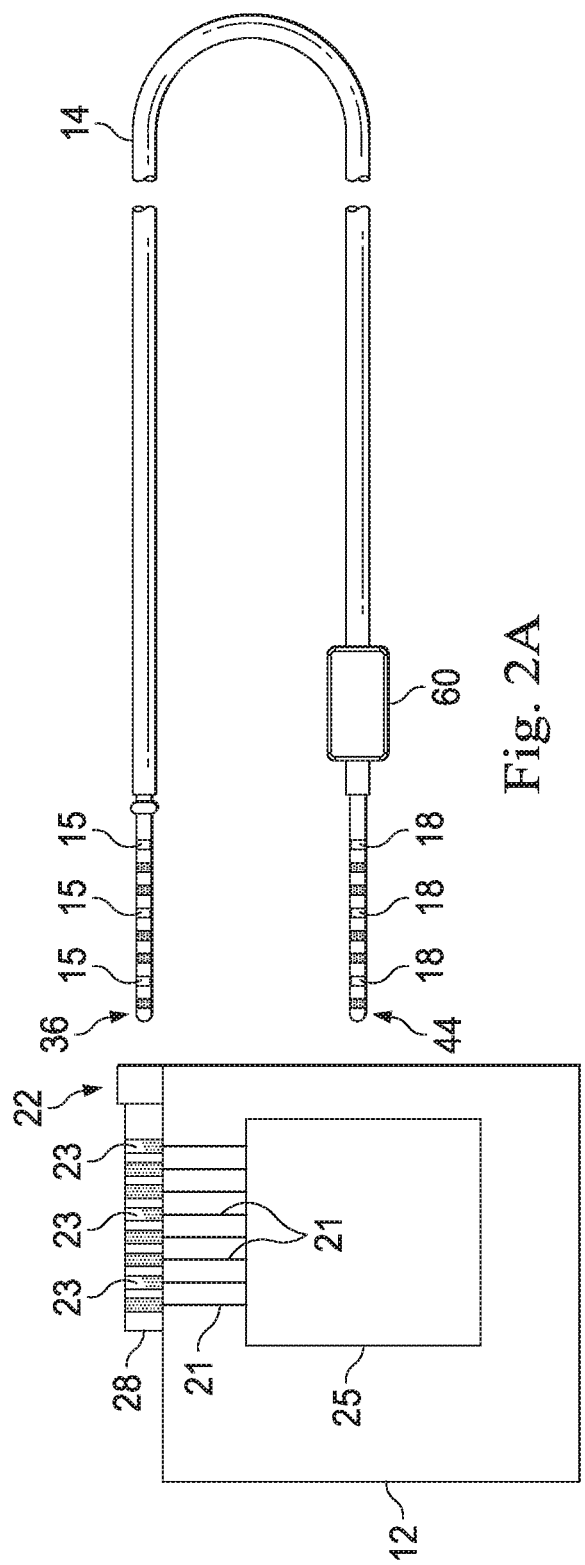

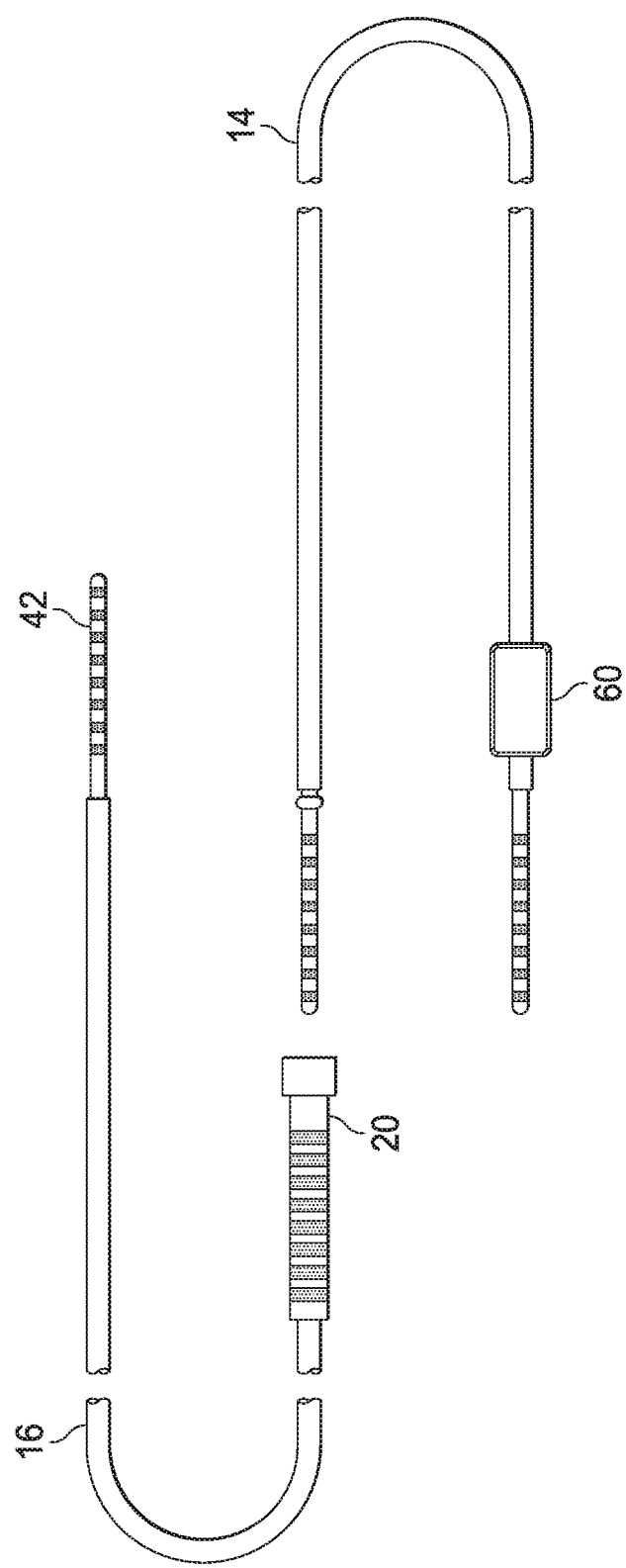

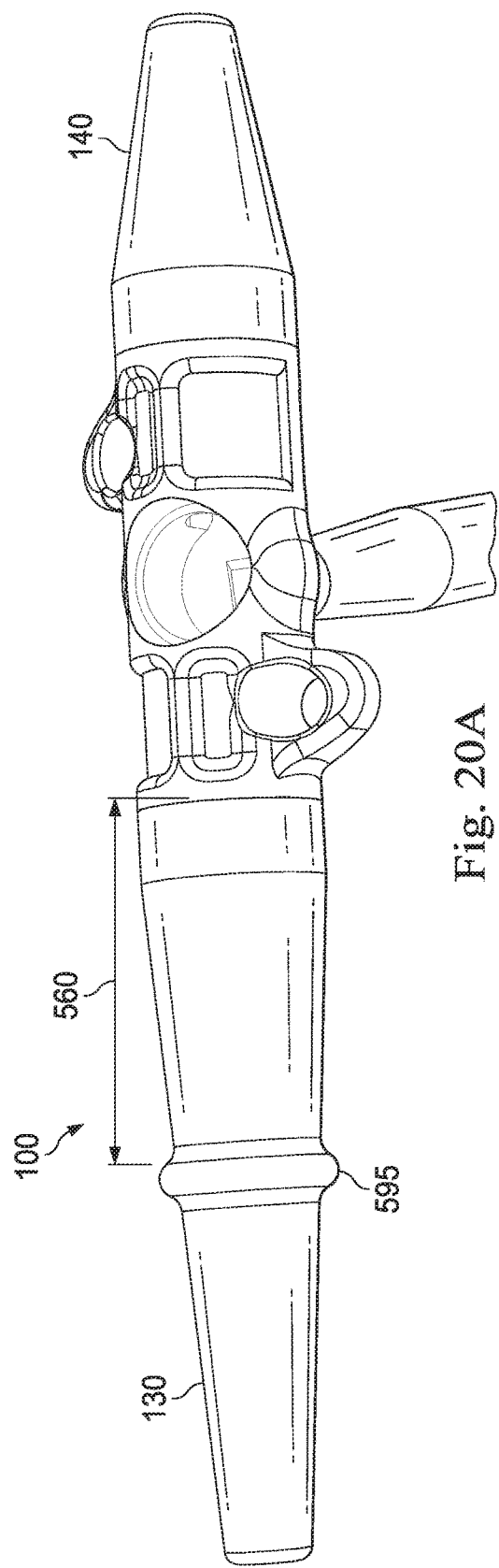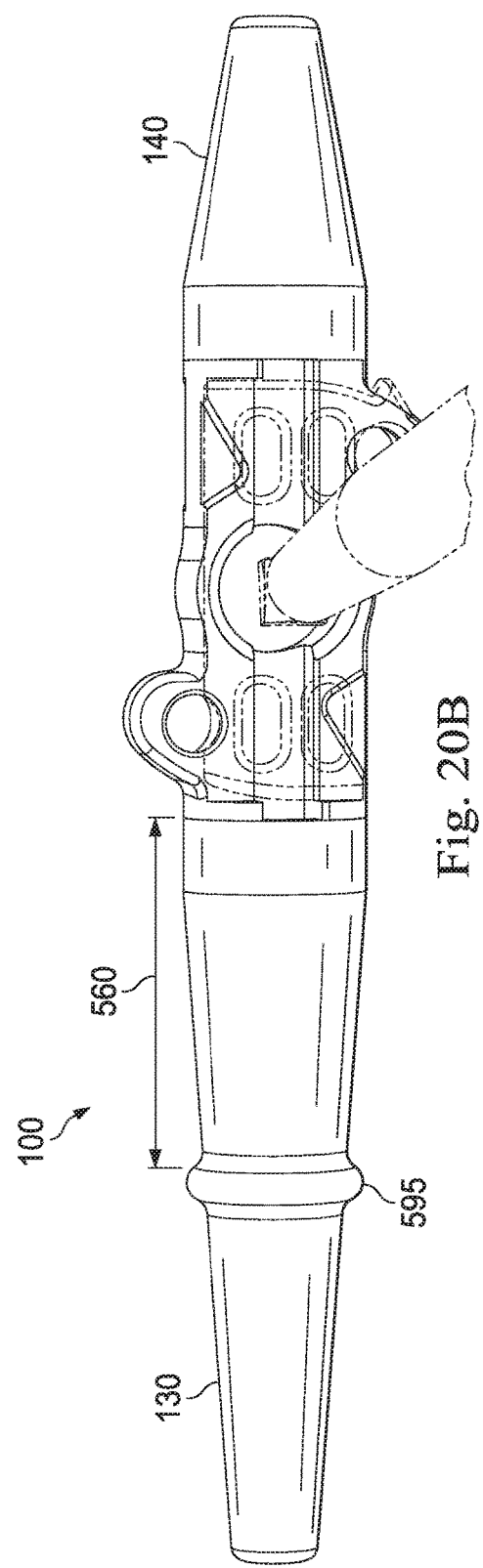

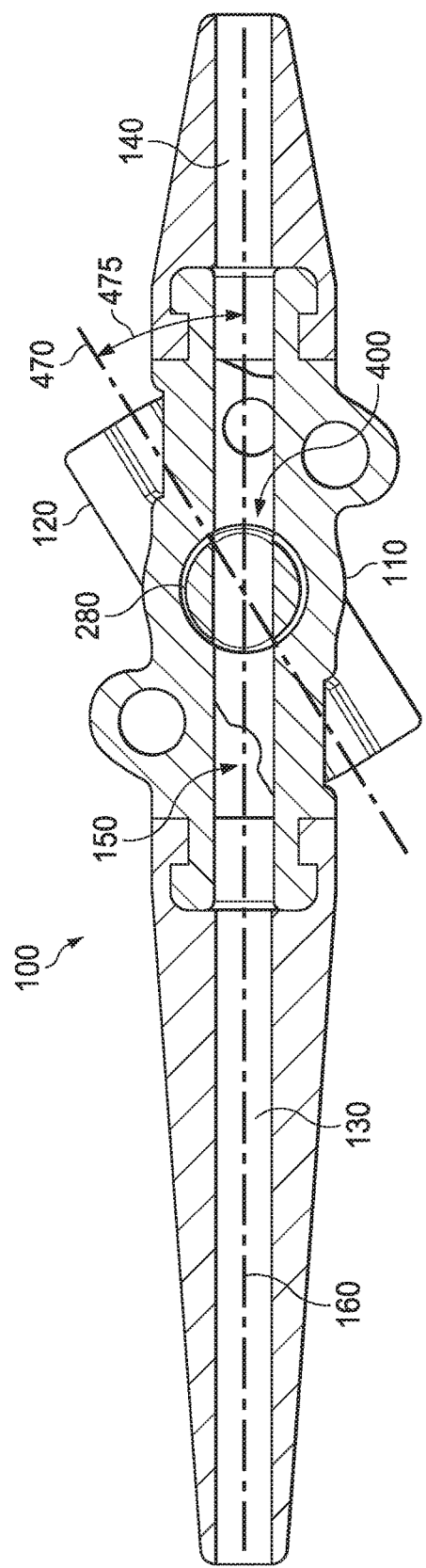

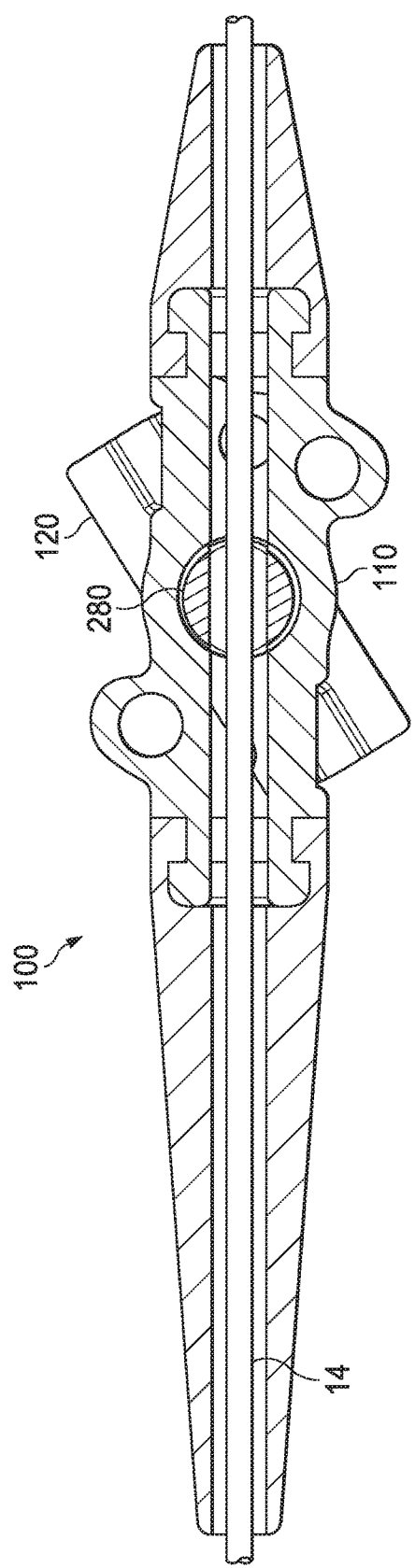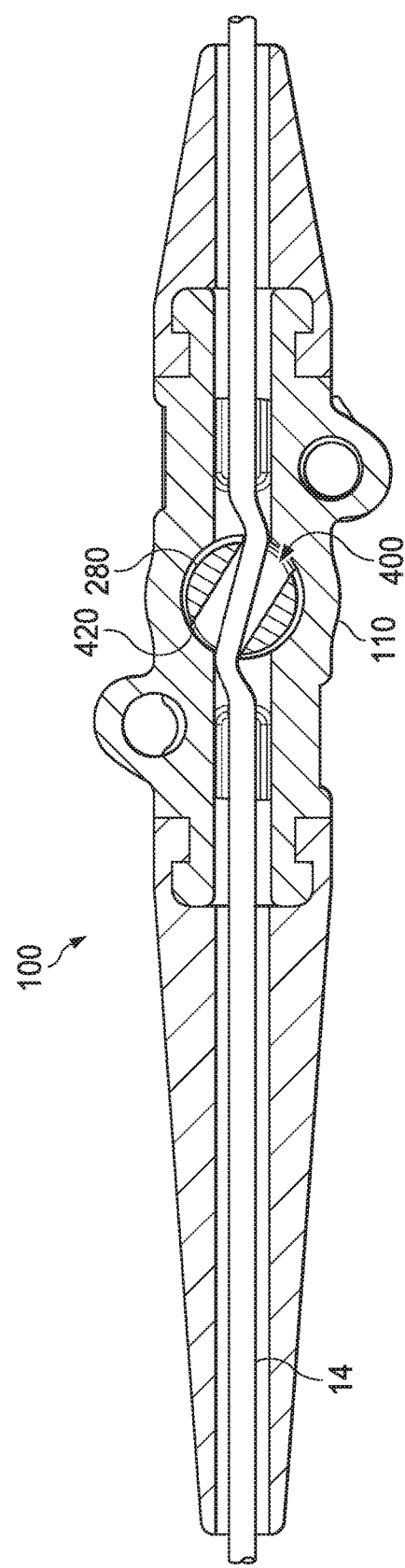

IMPLANTABLE ANCHOR LOCKING MECHANISM

PRIORITY DATA

This application claims benefit of U.S. Provisional Application No. 62/406,463 filed Oct. 11, 2016, which is incorporated herein by reference in its entirety.

FIELD

The present disclosure is directed to a method and apparatus that allows for electrical stimulation of body tissue, for example nerves. More specifically, this disclosure relates to a system, device, and method of anchoring an implantable medical electrical lead used for delivering the electrical stimulation to the body tissue.

BACKGROUND

Implantable medical electronic devices may include pulse generators (e.g., implantable pulse generators) capable of generating electrical stimulation. Implantable medical electronic devices may also include an implantable lead or leads that are used to transmit the electrical impulse to the targeted tissues of a patient's body. Examples of these implantable medical devices include cardiac pacemakers, and a number of related applications for cardiac rhythm management, treatments for congestive heart failure, and implanted defibrillators. Other applications for implantable pulse generators include neurostimulation with a wide range of uses such as pain control, nervous tremor mitigation, incontinent treatment, epilepsy seizure reduction, vagus nerve stimulation for clinical depression, and the like.

Typically, the electrical stimulation generated by an implantable pulse generator is delivered through one or more electrodes located on the implantable lead. To ensure that the electrical stimulation is delivered to the correct body regions, the implantable lead needs to be affixed to the tissue to prevent the movement of the implantable lead (and its electrodes) after the healthcare professional is satisfied with the electrical stimulation delivery. For example, an anchoring device may be used to hold the implantable lead therein, and then the anchoring device may be sutured to a nearby body tissue. This may be referred to as "anchoring" the implantable lead.

However, existing anchoring devices and methods of anchoring the implantable lead still have certain shortcomings. For example, existing anchoring devices may not allow the healthcare professional (e.g., a surgeon who is positioning the lead) easy visual access to the implantable lead positioned within the anchoring device. As another example, although existing anchoring devices may offer different configurations where the implantable lead may be moved or locked, the healthcare professional may inadvertently cause the anchoring device to switch back and forth between these different configurations, which may be undesirable. As yet another example, in locking the implantable lead (to prevent the movement of the lead inside the anchoring device), existing anchoring devices may cause damage to the implantable lead.

Therefore, although existing systems and methods for anchoring implantable leads are generally adequate for their intended purposes, they have not been entirely satisfactory in all respects.

SUMMARY

One aspect of the present disclosure involves a device for anchoring an implantable medical device inside a body. The device includes: an anchor body that includes an outer surface defining a first trough that extends along a first axis, the first trough being configured to receive a portion of the implantable medical device, wherein the first trough includes a cavity; and a locking member coupled to the anchor body and configured to rotate with respect to a second axis different from the first axis, such that the locking member is rotatable between a first position and a second position; wherein: the locking member includes a first member and a plurality of second members attached to the first member, the second members protruding outwardly from the first member and insert-able into the cavity to couple the locking member to the anchor body; the first member is configured to provide a cover for at least a portion of the first trough when the locking member is rotated to the second position; the second members define a second trough that is aligned with the first trough when the second members are inserted into the cavity and the locking member is rotated to the first position, so as to form an open path for the implantable medical device to move through the first and second troughs; and the second members block at least a portion of the first trough to define a tortuous path between the first trough and the second trough when the locking member is rotated to the second position, so as to restrict a movement of the implantable medical device through the first and second troughs.

Another aspect of the present disclosure involves a device for anchoring an implantable medical device inside a body. The device includes: an anchor body that includes an exterior surface defining an open channel that extends along a first axis, the open channel being configured to receive a portion of the implantable medical device; and a locking member coupled to the anchor body and configured to rotate between a first position and a second position with respect to a second axis different from the first axis, such that: in an unlocked configuration corresponding to the first position, the locking member cooperates with the anchor body to define an open path for the implantable medical device to move therethrough; and in a locked configuration corresponding to the second position, the locking member cooperates with the anchor body to restrict movement of the implantable medical device; wherein: the locking member includes a detent that provisionally locks the locking member in the second position by protruding into the open channel; and the anchor body includes recesses for seating the detent when the locking member is rotated into the first position, the seated detent provisionally locking the locking member in the first position.

Yet another aspect of the present disclosure involves a device for anchoring an implantable medical device inside a body. The device includes: an anchor body that includes an outer surface defining a first trough that extends along a first axis, the first trough being configured to receive a portion of the implantable medical device, wherein the first trough includes a cavity; and a locking member coupled to the anchor body and configured to rotate with respect to a second axis different from the first axis, such that the locking member is rotatable between a first position and a second position; wherein: the locking member includes a first member and a plurality of second members attached to the first member, the second members protruding outwardly from the first member and insert-able into the cavity; the first member is configured to provide a cover for at least a portion of the first trough when the locking member is rotated to the second position; the second members define a second trough that is aligned with the first trough when the second members are inserted into the cavity and the locking member is rotated to the first position, so as to form an open path for the implantable medical device to move through the first and second troughs; and the second members have at least one corner configured to engage the implantable medical device when the locking member is rotated to the second position, so as to restrict a movement of the implantable medical device without damaging the implantable medical device, the corner having a radius between 0.002 inches and 0.010 inches.

A further aspect of the present disclosure involves a method of anchoring an implantable medical device inside a patient. The method includes: placing an anchor for the implantable medical device inside the patient, the anchor including: an anchor body that includes an outer surface defining a first trough that extends along a first axis; and a locking member coupled to the anchor body, the locking member including a first member and a plurality of second members attached to the first member, the second members defining a second trough, the locking member being rotatable with respect to a second axis different from the first axis; inserting, while the locking member is rotated to a first position, the implantable medical device through an open path formed collectively by the first trough and the second trough; and rotating the locking member into a second position different from the first position, wherein the second members cooperate with the anchor body to engage with the implantable medical device while the locking member is rotated in the second position, so as to restrict a movement of the implantable medical device.

Yet a further aspect of the present disclosure involves a stimulation system. The system includes a pulse generator, an implantable lead electrically coupled to the pulse generator and a lead anchor device configured to slidably receive the lead in a first open configuration and configures to securely hold the lead in a second locked configuration. The anchor device including at least two components cooperatively defining a channel therebetween by aligned troughs.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In the figures, elements having the same designation have the same or similar functions.

FIG. 2A is a schematic illustration of an implantable pulse generator and a therapy delivery element in accordance with an embodiment of the present disclosure.

FIG. 2B is a schematic illustration of a lead extension and a therapy delivery element in accordance with an embodiment of the present disclosure.

FIGS. 17-19 and 20A-20B are perspective views of the anchoring device according to different embodiments of the present disclosure.

FIGS. 21-22 are different cross-sectional views of the anchoring device according to an embodiment of the present disclosure.

FIGS. 23-24 are different cross-sectional views of the anchoring device with a therapy delivery element positioned therein according to an embodiment of the present disclosure.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Before any embodiments of the invention are explained in detail, it is to be understood that the invention is not limited in its application to the details of construction and the arrangement of components or ordering of method steps set forth in the following description or illustrated in the following drawings. The invention is capable of other embodiments and of being practiced or of being carried out in various ways.

The description that follows highlights spinal cord stimulation (SCS) system, the treatment of pelvic floor disorders, and peripheral nerve field stimulation (PNFS) as non-limiting examples where an implantable medical device needs to be anchored. However, it is to be understood that the disclosure relates to any type of implantable therapy delivery system with one or more therapy delivery elements with one or more electrodes or sensors that need anchoring. For example, the present disclosure may be used as part of a pacemaker, a defibrillator, a cochlear stimulator, a retinal stimulator, a stimulator configured to produce coordinated limb movement, a cortical stimulator, a deep brain stimulator, microstimulator, or in any other neural stimulator configured to treat sleep apnea, shoulder sublaxation, headache, etc., where anchoring of an implantable device is desired. In other embodiments, one or more of the therapy delivery elements (that may need anchoring) may be a fluid or drug delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet other embodiments, one or more of the therapy delivery elements (that need anchoring) may be a medical electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes, but is not limited to, pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
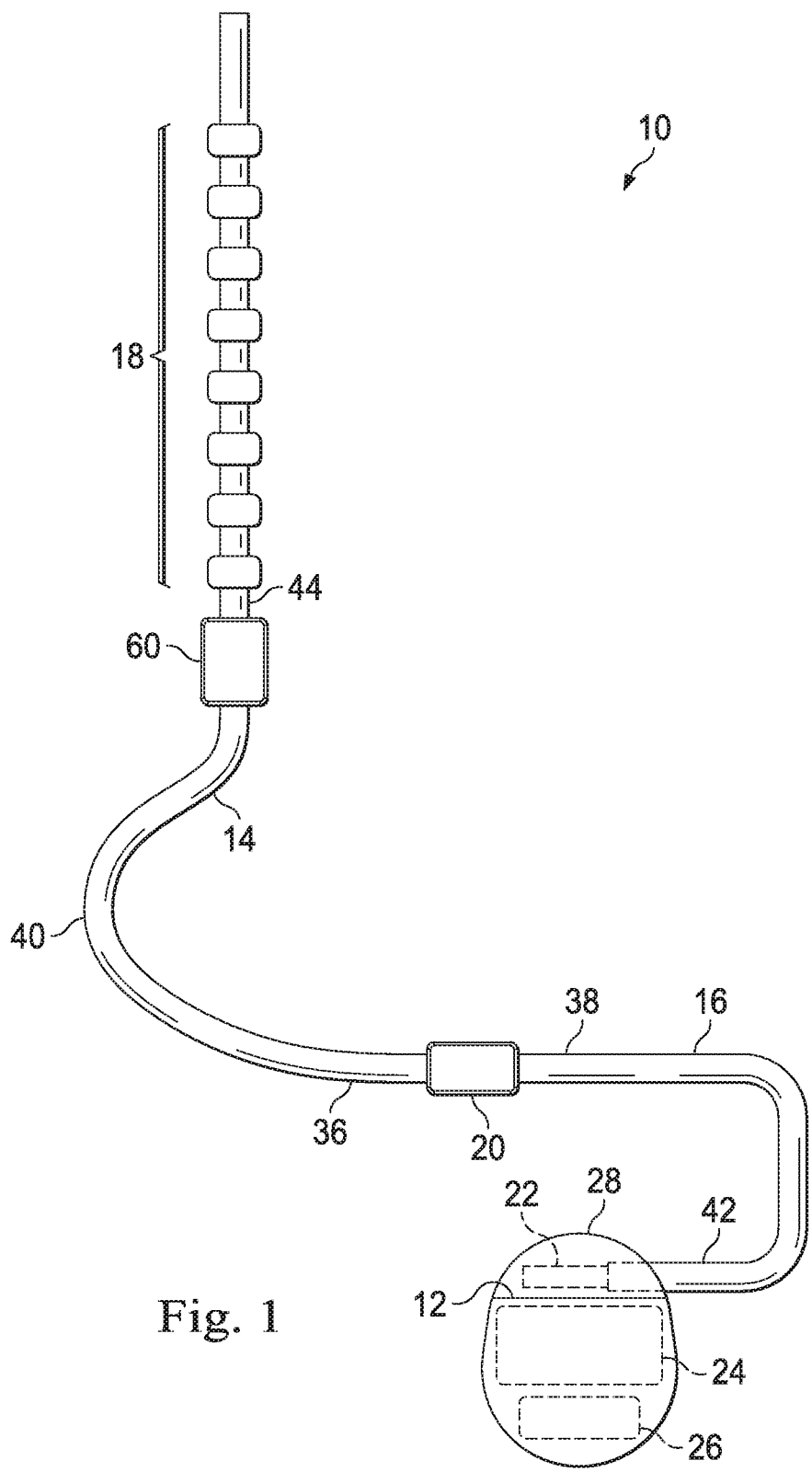
FIG. 1 is a schematic illustration of a therapy delivery system.

FIG. 1 illustrates a generalized therapy delivery system 10 that may be used in stimulation applications. The therapy delivery system 10 generally includes an implantable pulse generator 12 ("IPG"), an implantable therapy delivery element 14, which carries an array of electrodes 18 (shown exaggerated for purposes of illustration), an anchor 60, and an optional implantable extension lead 16. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter ranging between about 0.03 inches to about 0.07 inches and a length ranging between about 30 cm to about 90 cm for spinal cord stimulation applications. The lead body 40 may include a suitable electrically insulative coating, such as, a polymeric material (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium or stainless steel, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

FIG. 2A illustrates the therapy delivery element 14 including an anchor 60 positioned adjacent a distal end and one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22. In the embodiment illustrated in FIGS. 2A and 2B, the therapy delivery element 14 forms a medical electrical lead.

The connector assembly 22 includes a plurality of discrete contacts 23 located in the housing 28 that electrically couple contact rings 15 on the proximal end of the therapy delivery element 14. The discrete contacts 23 are electrically coupled to circuitry 25 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can be configured to independently deliver electrical impulses to each of the electrodes 18.

Alternatively, the therapy delivery element 14 can be coupled to the implantable pulse generator 12 through one or more lead extensions 16, as illustrated in FIG. 2B. The connector 20 at the distal end 38 of the lead extension 16 preferably includes a plurality of the contacts 23 configured in a manner similar to the connector assembly 22.

Figure 3:
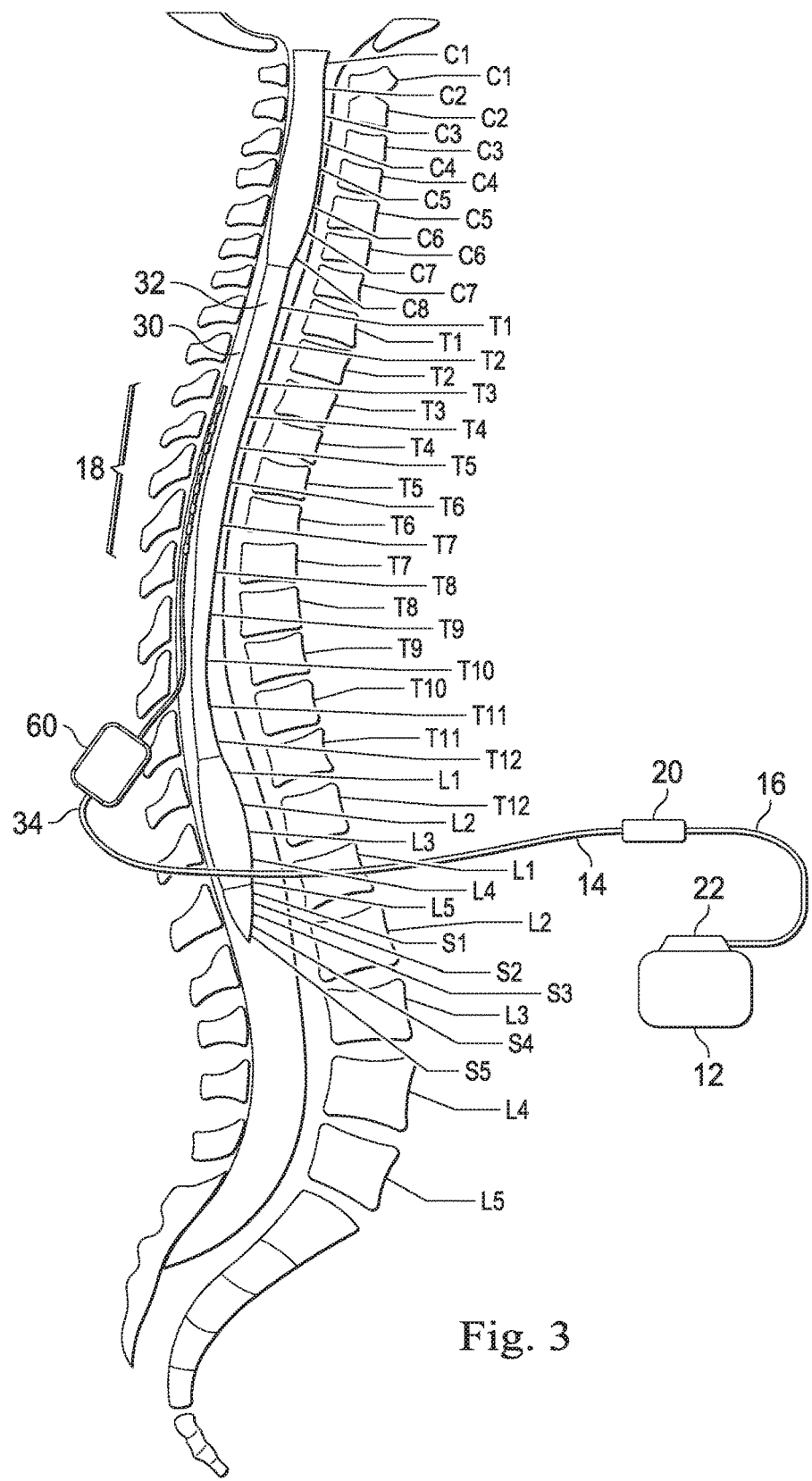
FIG. 3 is a schematic illustration of a therapy delivery system for spinal cord stimulation in accordance with an embodiment of the present disclosure.

To provide an example context, FIG. 3 illustrates the therapy delivery element 14 used for spinal cord stimulation (SCS). At least portions of therapy delivery element 14 is implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as the proximate sacral nerves. An anchor 60 may be used to secure the electrodes 18 in the desired location within a patient.

Figure 4:
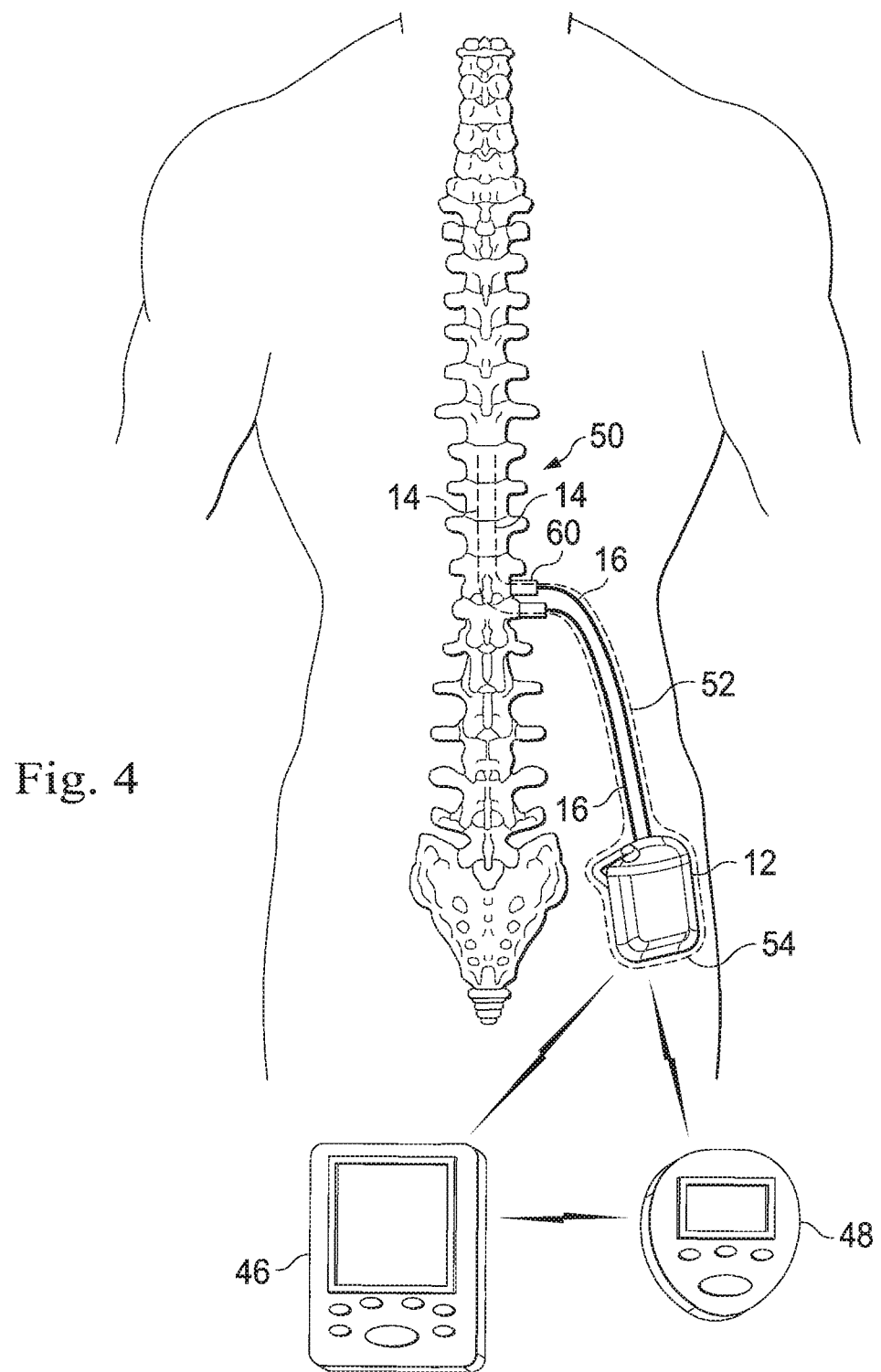
FIG. 4 is an alternate illustration of an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 4. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 4, the therapy delivery system 10 also may include a clinician programmer 46 and a patient programmer 48. Clinician programmer 46 may be a handheld computing device that permits a clinician to program neurostimulation therapy for a patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" may be used interchangeably, unless context indicates otherwise.

The therapy delivery elements 14 are typically fixed in place near the location selected by the clinician using suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner. Specific embodiments of the suture anchors 60 will be discussed in greater detail below.

Figure 5:
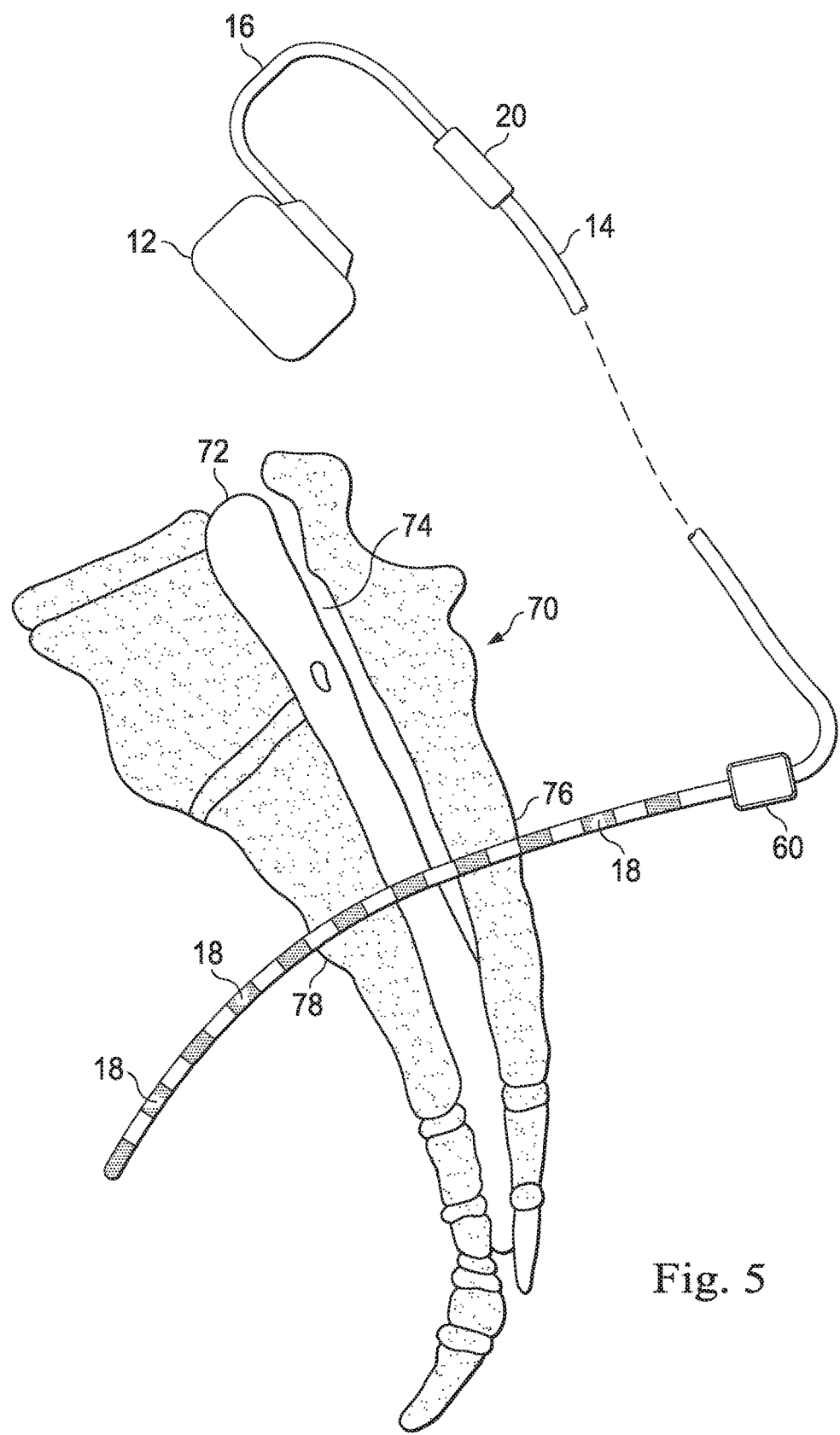
FIG. 5 is a schematic illustration of a therapy delivery system for treating pelvic floor disorders in accordance with an embodiment of the present disclosure.

To provide another example context, FIG. 5 illustrates the therapy delivery element 14 used for pelvic floor disorders, such as: urinary incontinence, urinary urge/frequency, urinary retention, pelvic pain, bowel dysfunction (constipation, diarrhea), erectile dysfunction, are bodily functions influenced by the sacral nerves. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles 72 within the sacrum 70. The sacrum 70, generally speaking, is a large, triangular bone situated at the lower part of the vertebral column, and at the upper and back part of the pelvic cavity. The spinal canal 74 runs throughout the greater part of the sacrum 70. The sacrum is perforated by the posterior sacral foramina 76 and anterior sacral foramina 78 that the sacral nerves 70 pass through.

Specifically, urinary incontinence is the involuntary control over the bladder that is exhibited in various patients. The therapy delivery element 14 is percutaneously implanted through the foramina 76, 78 of the sacral segment S3 for purposes of selectively stimulating the S3 sacral nerve 72. Stimulation energy is applied through the lead 14 to the electrodes 18 to test the nerve response. The electrodes 18 are moved back and forth to locate the most efficacious location, and the lead 14 is then secured by suturing the lead body and/or anchor 60 to subcutaneous tissue posterior to the sacrum 70 and attached to the output of a neurostimulator IPG 12.

Figure 6:
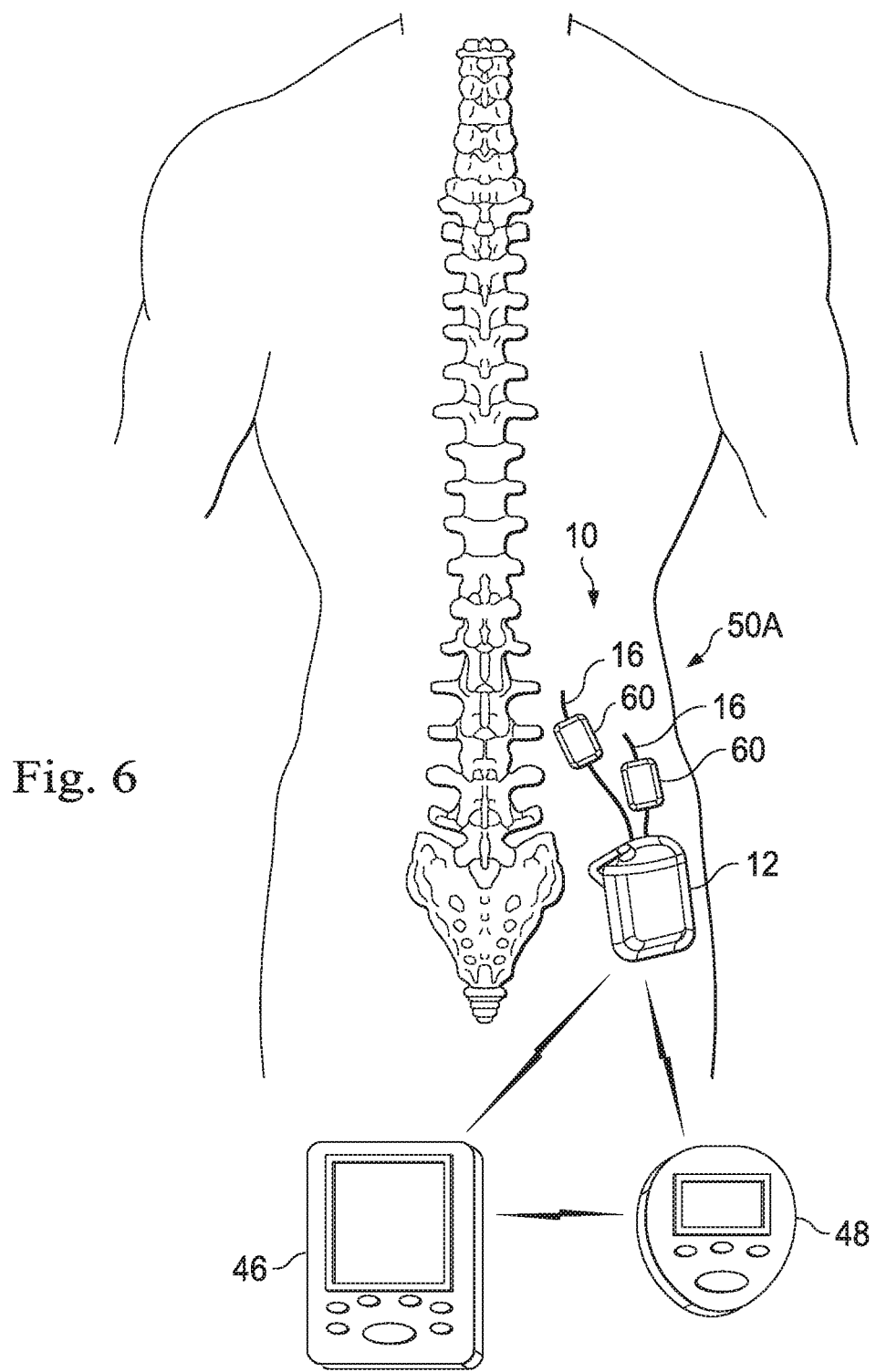
FIG. 6 is a schematic illustration of a therapy delivery system for peripheral nerve stimulation in accordance with an embodiment of the present disclosure.

To provide a further example context, FIG. 6 illustrates the therapy delivery element 14 used for delivering peripheral nerve field stimulation (PNFS) to a patient. Therapy delivery element 14 delivers PNFS from the implantable pulse generator 12 to the tissue of patient at target location 50A where patient experiences pain. Clinician programmer 46 and patient programmer 48 may communicate via wireless communication with the implantable pulse generator 12.

Therapy delivery element 14 may be implanted within or between, for example, intra-dermal, deep dermal, or subcutaneous tissue of patient at the location 50A where patient experiences pain. Subcutaneous tissue includes skin and associated nerves, and muscles and associated nerves or muscle fibers. In the illustrated example, location 50A is a region of the lower back. In other examples, the therapy delivery element 14 may extend from implantable pulse generator 12 to any localized area or dermatome in which patient experiences pain, such as various regions of the back, the back of the head, above the eyebrow, and either over the eye or under the eye, and may be used to treat failed back surgery syndrome (FBBS), cervical pain (e.g., shoulder and neck pain), facial pain, headaches supra-orbital pain, inguinal and pelvic pain, chest and intercostal pain, mixed pain (e.g., nociceptive and neuropathic), visceral pain, neuralgia, peroneal pain, phantom limb pain, and arthritis.

Regardless of the context in which the therapy delivery element 14 is used, the therapy delivery element 14 needs to be anchored (or otherwise secured) to a portion of the patient's body, so as to make sure the therapy delivery element 14 does not drift or migrate, which may be exacerbated by the patient's physical movements. Therefore, anchoring devices such as the suture anchors 60 are used to anchor the therapy delivery element 14. Various aspects of the present disclosure pertain to an anchoring device that offers improvements over conventional anchoring devices. Embodiments of the anchoring device according to the present disclosure are now discussed in more detail with reference to FIGS. 7-22.

Figure 7:
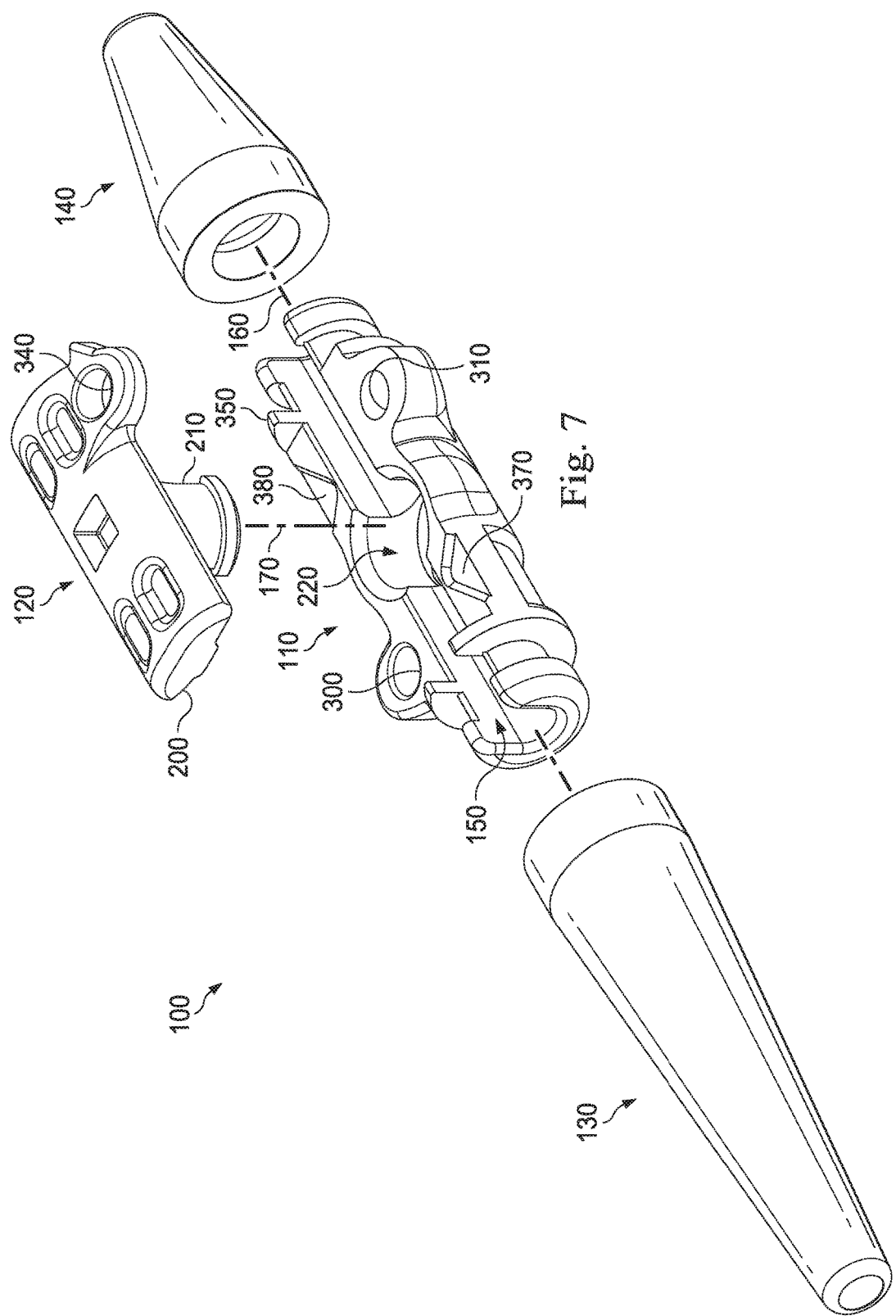
FIG. 7 is an exploded perspective view of an anchoring device according to one embodiment of the present disclosure.

Referring to FIG. 7, an exploded perspective view of an anchoring device 100 is illustrated. The anchoring device 100 is an embodiment of the suture anchors 60 discussed above. The anchoring device 100 includes an anchor body 110, a locking member 120, a distal strain relief 130, and a proximal strain relief 140. One or more of these components of the anchoring device 100 may be made of a translucent material, for example EIVA 500 PSU (Polysulfone).

The anchor body 110 includes an elongated open channel (or a trough) 150 that is defined by an outer surface of the anchor body 110. The open channel 150 extends along an axis 160. The distal strain relief 130 and the proximal strain relief 140 are also coupled to opposite ends of the anchor body 110 along the axis 160. The therapy delivery element 14 can be inserted into the open channel 150.

The locking member 120 is coupled to the anchor body 110 along an axis 170. In more detail, the locking member 120 includes a member 200 and one or more members 210 attached to, and protruding outwardly from, the member 200. The members 210 protrude along the axis 170 and are inserted into a cavity 220 in the open channel 150 when the locking member 120 is coupled to the anchor body 110. The members 210 are resiliently displaceable inwardly for insertion into opening 220 and spring resiliently outwardly once flanges 211 extend beyond opening 220. Flanges 211 engage the lower side of body 110 to retain locking member 120 in position. The locking member 120 is rotatable (e.g., by a healthcare professional such as a surgeon) with respect to the axis 170. In an embodiment, the locking member 120 is rotatable between an unlocked position (also referred to as an open position) and a locked position (also referred to as a closed position). When the locking member 120 is rotated into the unlocked position, the locking member 120 and the anchor body 110 cooperate to define an open path for the therapy delivery element 14, such that the therapy delivery element 14 can be moved freely along the open channel 150. In other words, the healthcare professional can reposition or adjust the placement of the therapy delivery element 14 when the locking member 120 is rotated into the unlocked position. When the locking member 120 is rotated into the locked position, the locking member 120 and the anchor body 110 cooperate to define a tortuous path for the therapy delivery element 14 (see FIG. 24), such that the movement of the therapy delivery element 14 is restricted inside the open channel 150. In this manner, the therapy delivery element 14 is "anchored" to the patient's body after the anchoring device 100 is sutured to nearby tissue.

Figure 8:
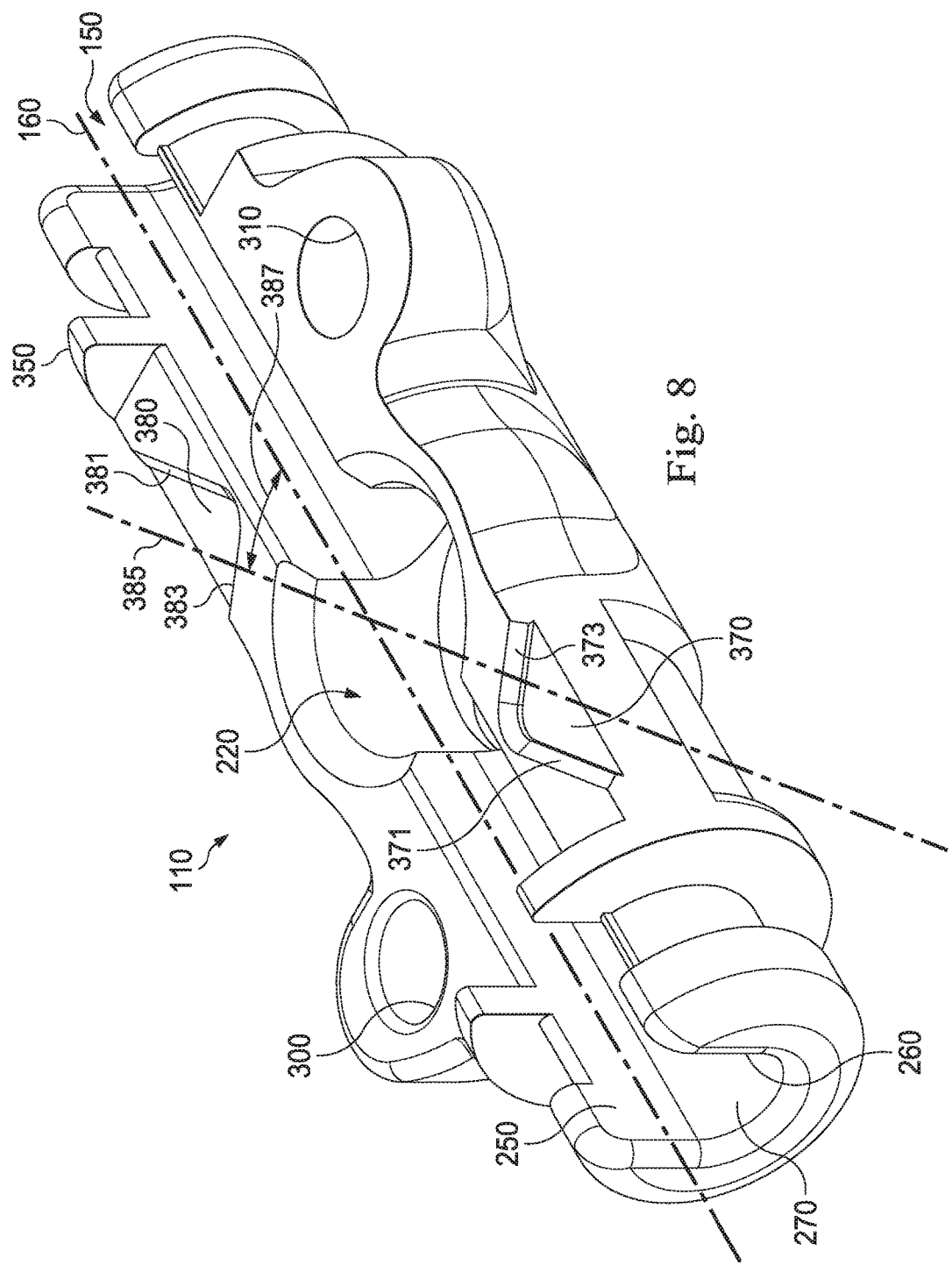
FIG. 8 is a perspective view of an anchor body of the anchoring device according to one embodiment of the present disclosure.
Figure 9:
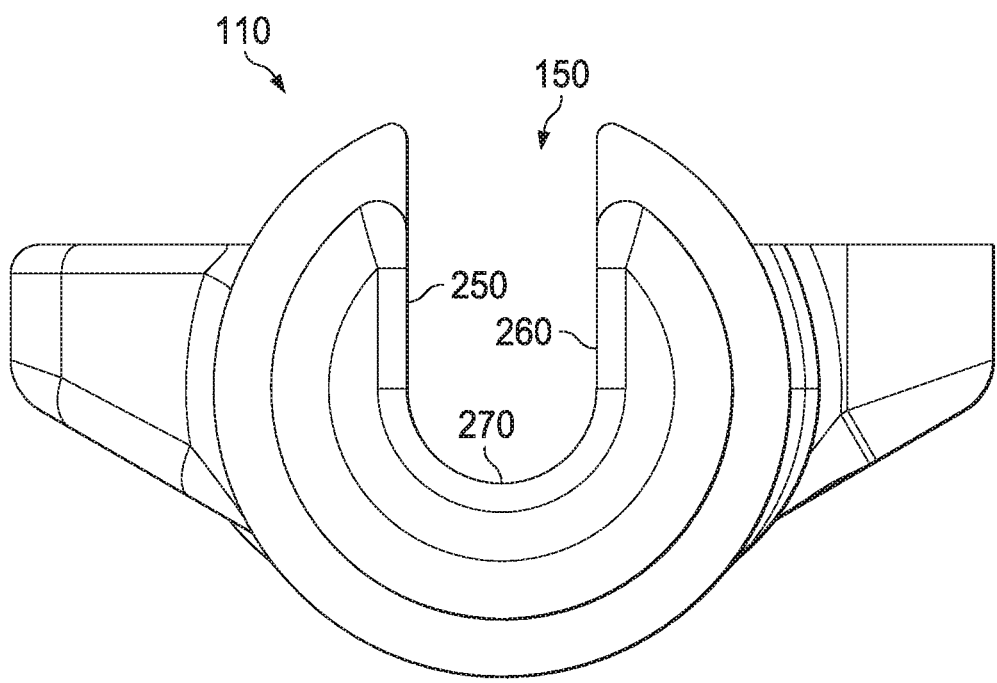
FIG. 9 is an end view of the anchor body of the anchoring device according to an embodiment of the present disclosure.
Figure 10:
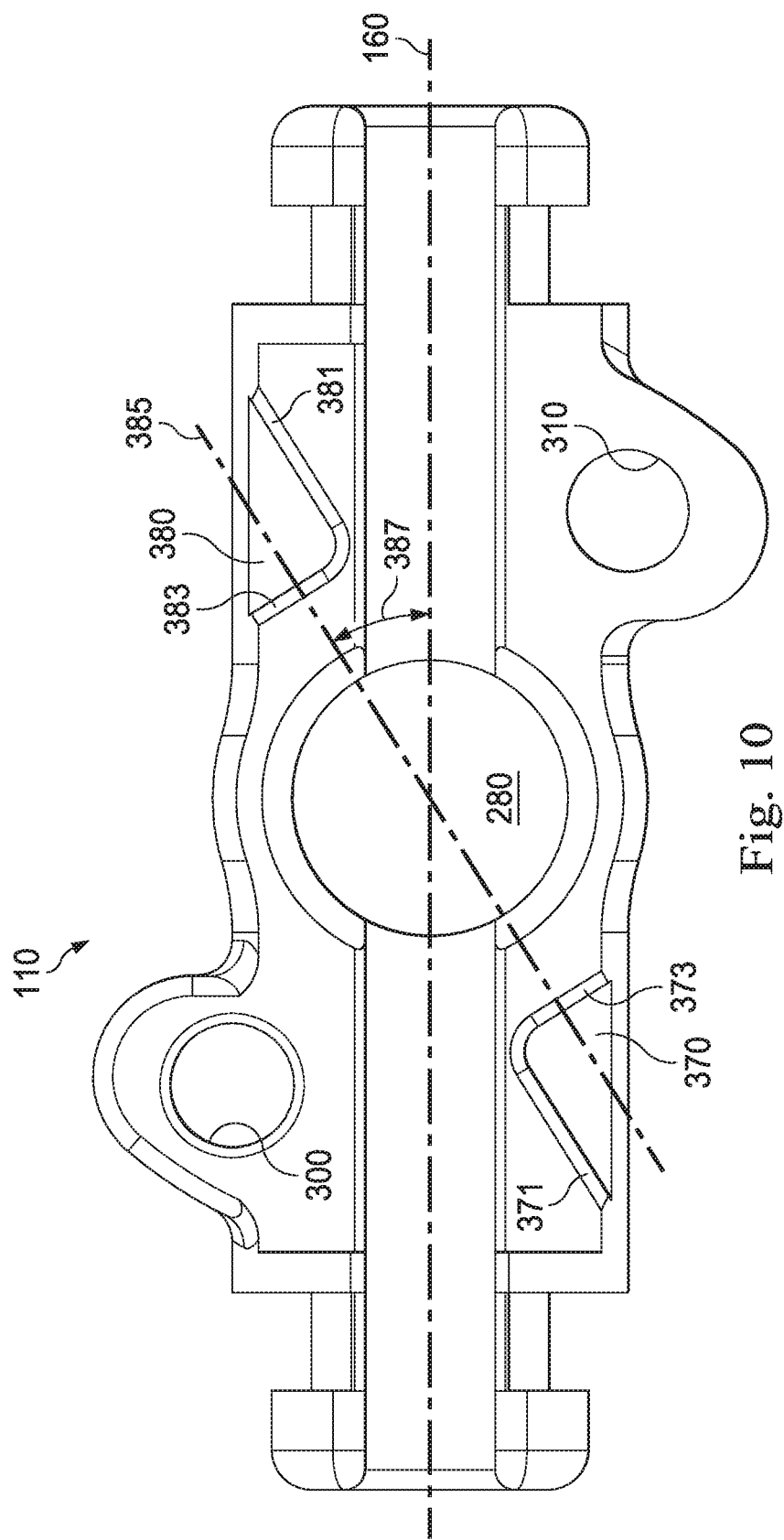
FIG. 10 is a planar view of the anchor body of the anchoring device according to embodiments of the present disclosure.

The mechanical structural features of the anchor body 110 are now discussed in more detail with reference to FIGS. 8-10. Specifically, FIG. 8 is a perspective view of the anchor body 110, FIG. 9 is an end view (looking along the axis 160) of the anchor body 110, and FIG. 10 is a planar view of the anchor body 110 (looking along the axis 170). The open channel 150 discussed above is more clearly illustrated in FIGS. 8 and 9. The open channel 150 is a recess that is defined by an outer surface or exterior surface of the anchor body 110. The open channel 150 is configured to receive an elongated medical device such as the therapy delivery element 14, for example an implantable lead having electrodes located thereon. Whereas some conventional anchoring devices use a circumferentially enclosed (in a cross-sectional view) lumen to receive an elongated medical device, the open channel 150 is open in at least one side/direction, for example in the direction facing the locking member 120. The openness of the channel 150 is easier to fabricate, allows for easier placement, permits visual inspection of the lead and offers better maneuverability of the therapy delivery element 14.

In the illustrated embodiment, the open channel 150 is a U-shaped trough (referred interchangeably with the open channel 150 hereinafter), which is more clearly shown in the cross-sectional view of FIG. 9. For example, the U-shaped trough 150 has a side wall 250, a side wall 260 opposing the side wall 250, and a floor 270 joining the side walls 250 and 260. In this embodiment, the side walls 250 and 260 are generally planar but faces substantially parallel to each other, and the floor 270 is curved, thereby creating the U-shaped cross-sectional profile of the open channel 150. However, it is understood that the open channel 150 is not limited to this specific cross-sectional profile. In other embodiments, the side walls 250 and 260 may be non-planar, and/or the floor 270 may be non-curved as well. Furthermore, there need not be a definite demarcation between the floor 270 and the side walls 250/260.

Referring to FIG. 8, the open channel 150 also includes a cavity 220. The cavity 220 is configured to receive the protruding members 210 of the locking member 210 (discussed above with reference to FIG. 7). As will be discussed in greater detail below, the rotation of the protruding members 210 inside the cavity 220 will permit or restrict the movement of the therapy delivery element 14. To facilitate the visual inspection of the therapy delivery element 14 inside the anchoring device 100, a window 280, which is defined by an opening or recess, of the anchor body 110 is also made to be at least partially transparent when viewed from a side opposing the locking member 120, as shown in the planar view of FIG. 10. In other words, the healthcare professional may visually inspect the anchor body 110 from the direction opposing the locking member 120, while the therapy delivery element 14 is located inside the anchor body 110. The transparency of the anchor body 110 allows the healthcare professional to see whether the therapy delivery element 14 is in the locked position or in the unlocked position, for example.

The cavity 220 is located at a middle portion of the anchor body 110 in the illustrated embodiment, but it is understood that the cavity 220 may also be located elsewhere in the anchor body 110. In addition, although the cavity 220 is configured to have a rounded top view profile in the illustrated embodiment, the cavity 220 may be configured to have different top view profiles in alternative embodiments, for example a square/rectangular top view profile. Furthermore, the window 280 of the anchor body 110 generally corresponds to the cavity 220 in the illustrated embodiment, but this is not intended to be limiting either. In alternative embodiments, the window 280 may exceed the planar view area of the cavity 220, or vice versa.

Referring to FIGS. 7-8 and 10, the anchor body 110 also includes a distal suture loop 300 and a proximal suture loop 310. The distal suture loop 300 and the proximal suture loop 310 each include a respective opening through which a stitch can be made. In some embodiments, the anchor body 110 can be sutured down to a nearby body tissue via the distal suture loop 300, without needing the proximal suture loop 310 to be sutured. As such, the movement of anchor body 110 itself is prevented.

Meanwhile, the therapy delivery element 14 can still slide through the open channel 150 when the locking member 120 is rotated into the unlocked or open position. As discussed later, the suture loop 300 only interacts with loop 310. In other words, the locking member 120 is movably independent from the distal suture loop 300, since the suturing down of the anchor body 110 through the distal suture loop 300 does not prevent the manipulation of the locking member 120. In this manner, the healthcare professional may reposition the therapy delivery element 14 even after the anchoring device 100 has been sutured to surrounding tissue.

The proximal suture loop 310 will be aligned with a proximal suture loop 340 located on the locking member 120 when the locking member 120 is rotated into the locking position, as will be discussed in greater detail below. The alignment of these proximal suture loops 310 and 340 provides visual confirmation that the anchoring device 100 is now in the locked position. The alignment of the proximal suture loops 310 and 340 will allow stitches to be made through the aligned proximal suture loops, which enables the rest of the anchoring device 100 to be sutured to nearby tissue after the positioning of the therapy delivery element 14 has been finalized.

Referring to FIGS. 7-8, the anchor body 110 also includes a protruding tab 350. The protruding tab 350 protrudes in a direction toward the locking member 120. In some embodiments, a portion of the surface of the protruding tab is coplanar with the side wall 250 of the open channel 150, though it is understood that this may not be the case for alternative embodiments. The protruding tab 350 interacts with a flange of the locking member 120 to prevent further rotation of the locking member 120 beyond the open/unlocked position and away from the closed/locked position. This will be discussed below in greater detail when the mechanical structure of the locking member 120 is discussed.

The anchor body 110 also includes recesses 370 and 380, which are also defined by the outer/exterior surface of the anchor body 110. Recesses 370 and 380 are formed by side walls 371 and 381 extend along axis 385 and intersecting end walls 373 and 383. In the illustrated embodiment, the axis 385 is at an angle 387 with respect to axis 160. In some embodiments, the angle 387 is in a range from about 20 degrees to about 40 degrees, for example 30 degrees. The recesses 370 and 380 are indentations in the anchor body 110. The recesses 370 are 380 are each configured to receive a respective detent 450 and 460 located on the locking member 120. The detents will provisionally lock the locking member 120 in the open/unlocked position by protruding into the recesses 370 or 380, so as to prevent inadvertent rotation of the locking member 120 back into the locked position. The interaction between the recesses 370/380 and the detents of the locking member 120 will also be discussed below in greater detail when the mechanical structural details of the locking member 120 are discussed. It is understood that although two recesses 370/380 are implemented in the embodiment illustrated herein, the anchor body 110 may include a different number of recesses (e.g., one, three, four, etc.) in alternative embodiments.

Figure 13:
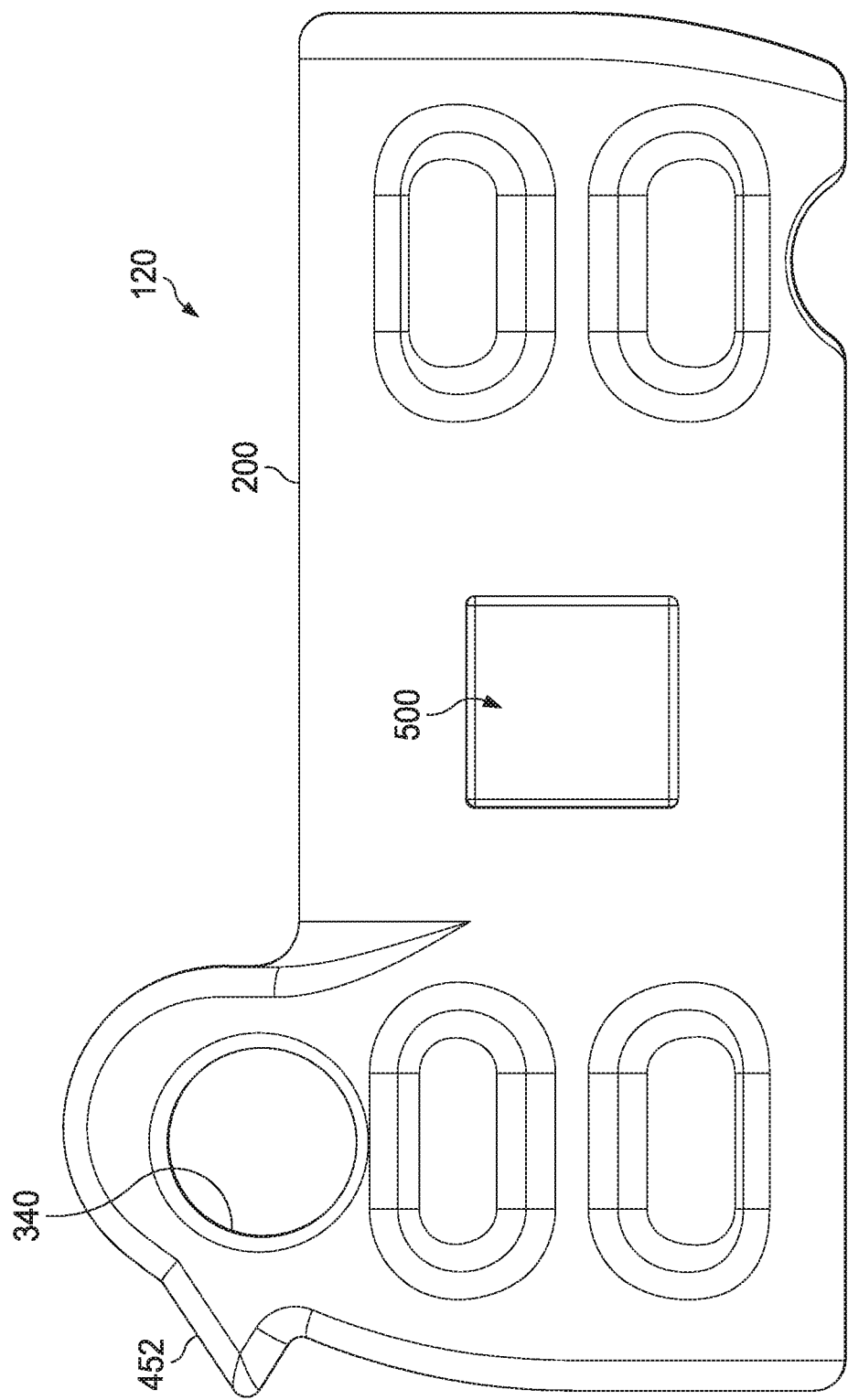
FIGS. 13-14 are different planar views of the locking member of the anchoring device according to an embodiment of the present disclosure.
Figure 14:
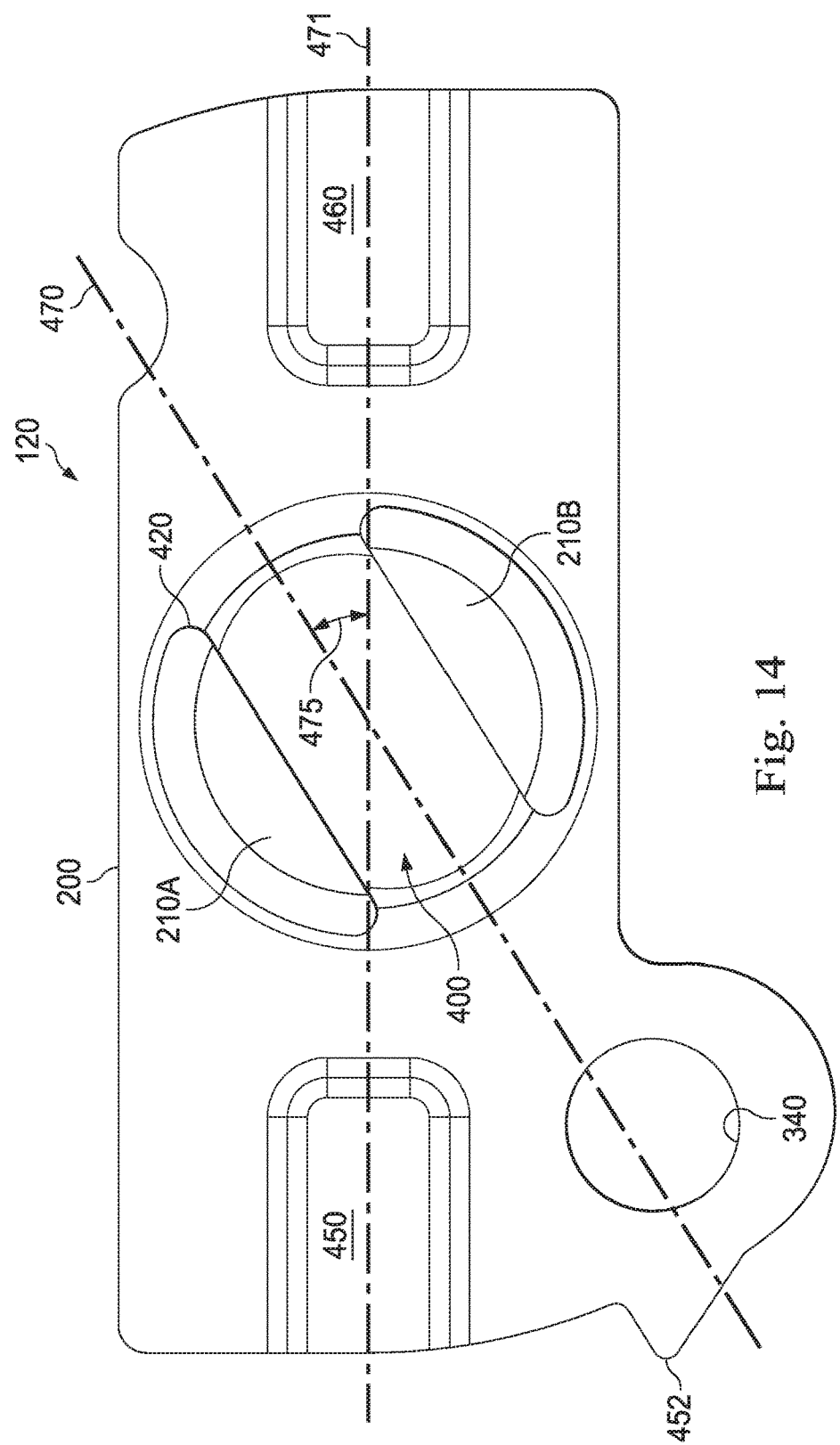
Figure 15:
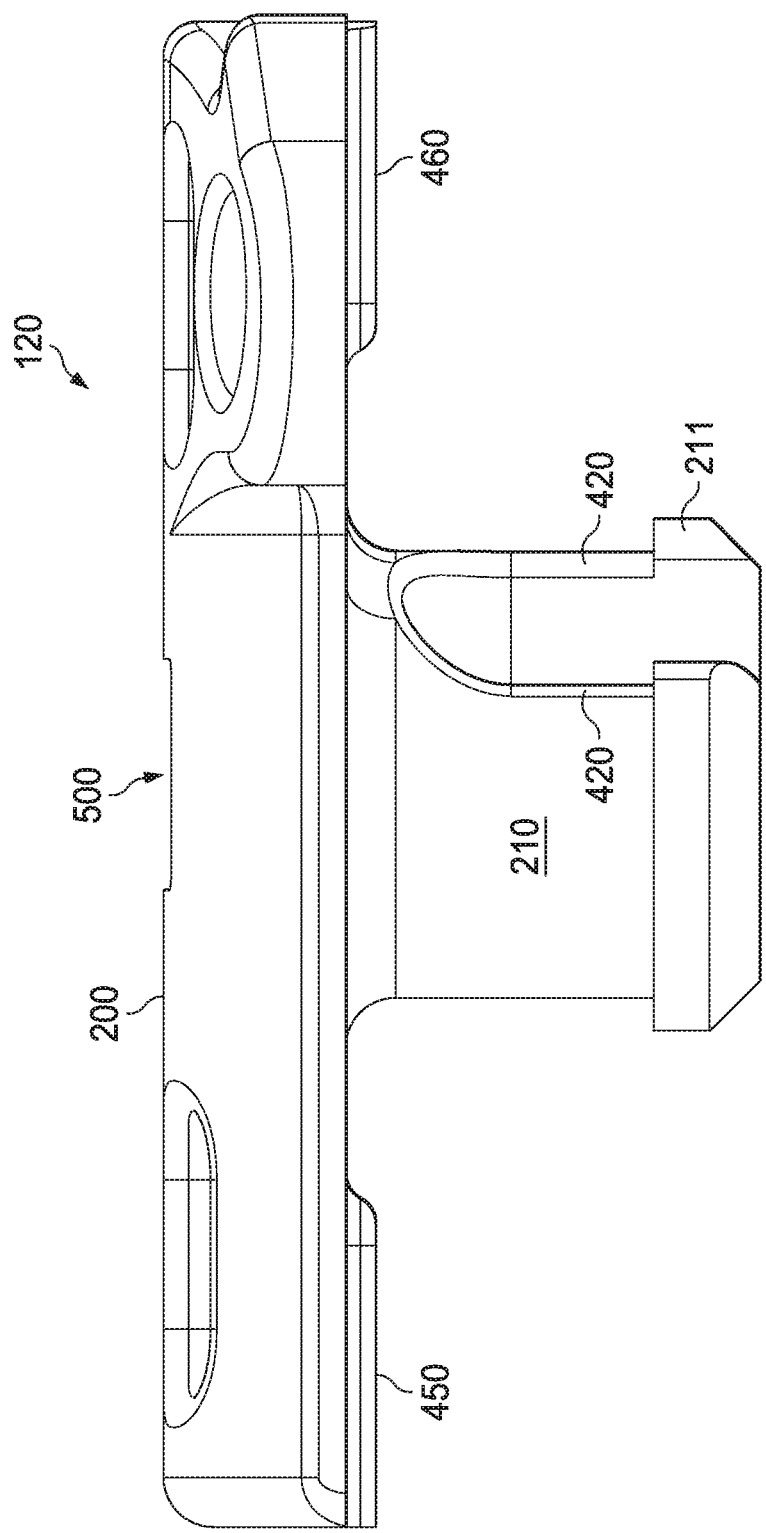
FIG. 15 is a side view of the locking member of the anchoring device according to an embodiment of the present disclosure.

The mechanical structural details of the locking member 120 will now be discussed in greater detail with reference to FIGS. 11-15. Specifically, FIGS. 11-12 are different perspective views of the locking member 120, FIG. 13 is a top planar view (looking along the axis 170 of FIG. 17 in a direction toward the anchor body 110) of the locking member 120, FIG. 14 is a bottom planar view (looking along the axis 170 of FIG. 17 in a direction away the anchor body 110 toward the locking member 120) of the locking member 120, and FIG. 15 is a side view of the locking member 120.

Figure 11:
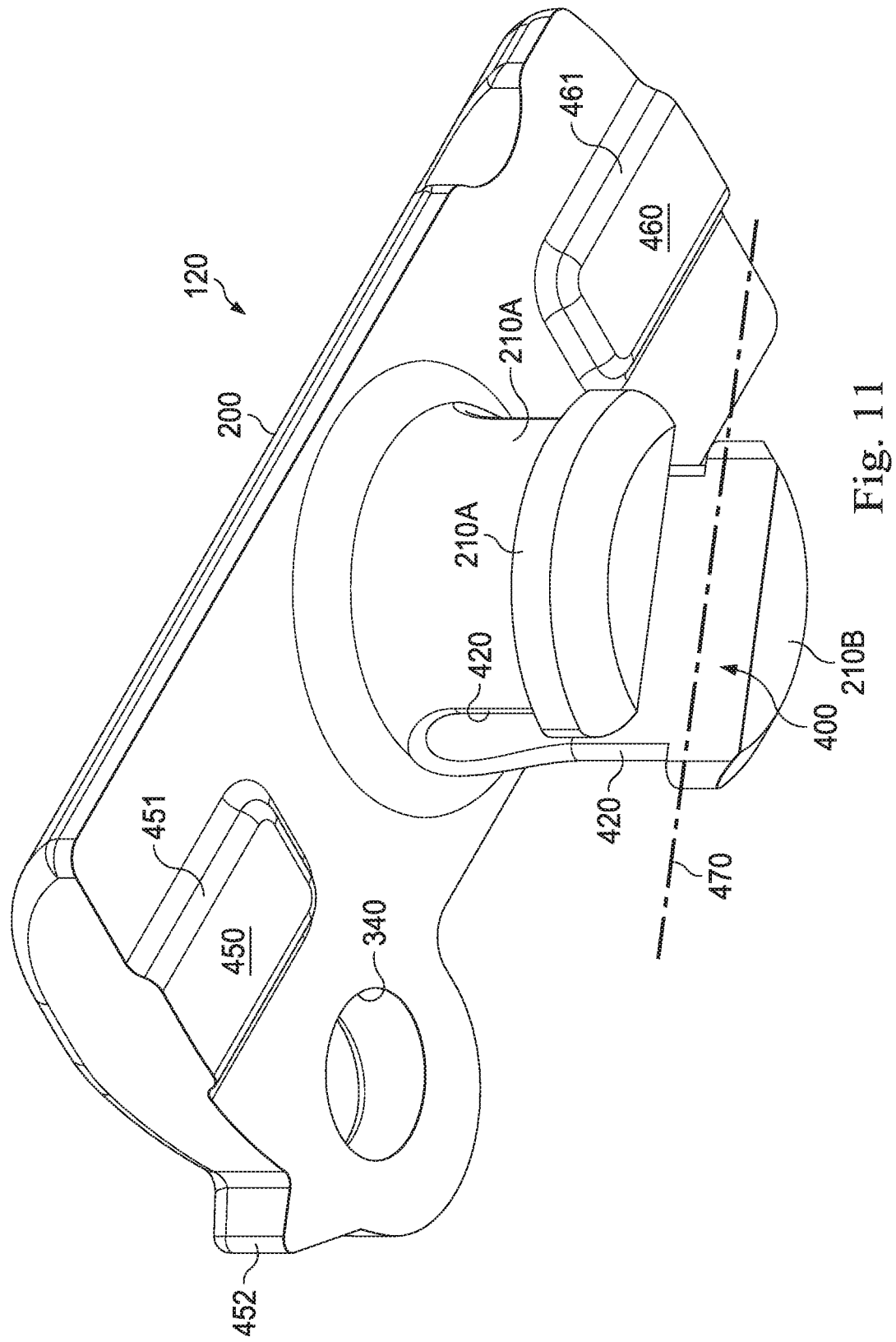
FIG. 11 is a perspective view of a locking member of the anchoring device according to an embodiment of the present disclosure.
Figure 12:
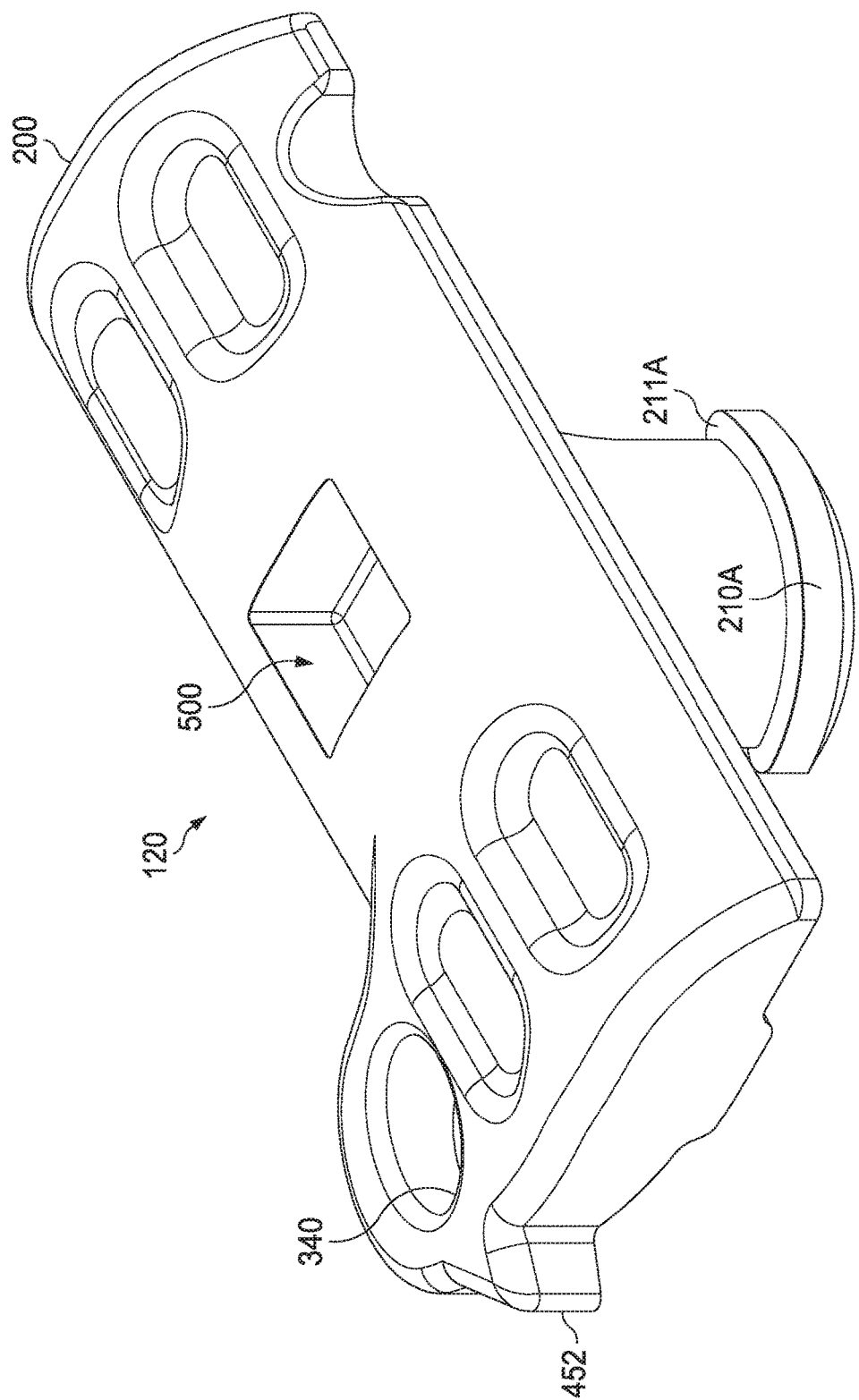
FIG. 12 is another perspective view of the locking member of the anchoring device according to an embodiment of the present disclosure.

As shown in FIGS. 11 and 12, the locking member 120 includes the member 200 and one or more protruding members 210 that are attached to the member 200 and protrude outwardly away from the member 200 (protruding in the direction defined by the axis 170 of FIG. 7). In the illustrated embodiment, there are two of such protruding members (labeled as 210A and 210B), though it is understood that other numbers (e.g., three, four, etc.) of protruding members may be implemented in alternative embodiments. In this embodiment, the two protruding members 210A/210B collectively define a trough 400 extending along axis 470. A planar view of the trough 400 is also shown in FIG. 14. In the illustrated embodiment, the trough 400 has a U-shaped cross-sectional profile that is oriented in a direction extending along axis 470 at an angle 475 with respect to axis 471. In some embodiments, the angle 475 is between about 20 degrees and about 40 degrees, for example 30 degrees. It is understood that the U-shaped cross-sectional profile of the trough 400 is not intended to be limiting, and that it may have different cross-sectional profiles in alternative embodiments. It is also understood that, when the anchoring device 100 is assembled, the "floor" 270 of the open channel 150 will face upwards, whereas the "floor" of the trough 400 (a floor joining the protruding members 210A and 210B) will face downwards. In other words, the floor of the open channel 150 and the floor of the trough 400 are facing opposite directions when the anchoring device 100 is assembled.

As discussed above, the locking member 120 can be rotated with respect to the axis 170 between the locked position and the unlocked position. In more detail, once the protruding members 210A/210B are inserted into the cavity 220 of the open channel 150 of the anchor body 110, the rotation of the locking member 120 changes the alignment of the trough 400 with the open channel 150. When the locking member 120 is rotated to the unlocked position, the trough 400 is aligned with the open channel 150. That is, the trough 400 also extends along the axis 160 along which the open channel 150 extends, and the axis 470 of trough 400 is substantially aligned with axis 160 such that the open channel 150 and trough 400 collectively form an open path for the therapy delivery element 14 to move therethrough. This allows the healthcare professional to reposition the therapy delivery element 14 inside the anchoring device 100 (e.g., by sliding the therapy delivery element 14 through the open channel 150).

In comparison, when the locking member 120 is rotated to the locked position with axis 471 aligned with axis 160, the trough 400 is misaligned with the open channel 150. In the illustrated embodiment the angle of misalignment between axis 160 and axis 471 is approximately 30 degrees In this manner, the members 210A/210B block at least a portion of the open channel 150 to define a tortuous path between the trough 400 and the open channel 150. The tortuous path restricts movements of the therapy delivery element 14 through the trough 400 and/or the open channel 150. For example, the tortuous path may cause the therapy delivery element 14 to come into physical contact with the side walls 250/260 of the open channel 150 and the members 210A/210B that define the trough 400. In other words, the open channel may be reduced to a size that is smaller than the diameter of the element 14 such that the therapy delivery element 14 may be "pinched" between the side walls 250/260 and the members 210A/210B. The "pinching" of the therapy delivery element 14 means that the therapy delivery element 14 has been "locked", so that it cannot be freely moved along the open channel 150. This may be done when the healthcare professional has finished repositioning the therapy delivery element 14, and migration/movement of the therapy delivery element 14 is no longer desired. At that point, the proximal suture loop 340 located on the locking member 120 is aligned with the proximal suture loop 310 located on the anchor body 110. The healthcare professional may then suture (via the aligned proximal suture loops 310 and 340) the anchoring device 100 to nearby tissue.

One potential problem with using the members 210A/210B to "lock" the therapy delivery element 14 is that, since the movement of the therapy delivery element 14 is restricted via physical contact with the member 210A/210B, the therapy delivery element 14 may be damaged by such physical contact, for example if the member 210A/210B "pinches" the therapy delivery element 14 with too much force or the amount of element 14 deformation is beyond the resilient limit of the device to recover. Thus, to prevent potential physical damage to the therapy delivery element 14, the members 210A and 210B may each be configured to have blunted corners 420. For example, each corner 420 may have a rounded or non-orthogonal shape. The blunted corners 420 help alleviate the stress or pressure delivered to the therapy delivery element 14 by the members 210A/210B, which will reduce the likelihood of the therapy delivery element 14 being physically damaged.

However, the corners 420 need sufficient sharpness to retain the lead in the desired position The roundedness or sharpness of the members 210A/210B may be measured or indicated by a radius. In some embodiments, the radius is in a range between 0.002 inches and 0.010 inches. In some embodiments, the radius is in a range between 0.004 inches and 0.006 inches. In some embodiments, the radius is about 0.005 inches. These numerical ranges or values of the radius are specifically configured such that the members 210A/210B can effectively pinch the therapy delivery element 14, having an outer diameter between about 0.055" and about 0.060", to restrict its physical movement, while also not causing physical damage to the therapy delivery element 14.

As shown in FIGS. 11, 14, and 15, the locking member 120 includes one or more protruding detent structures, for example detents 450 and 460. Although two detents 450/460 are implemented for the illustrated embodiment, other numbers of detents (e.g., one, three, four, etc.) may be implemented on the locking member 120 in alternative embodiments. The detents 450 and 460 are protrusions on the member 200 and protrude in the same direction as the members 210A/210B and have slightly angled side walls 451/461. The detents 450/460 facilitate the provisionally locking of the locking member 120 into the locked position, as well as the unlocked position.

For example, when the locking member 120 is rotated into the unlocked position (forming an open path for the therapy delivery element 14 inside the open channel 150), the detent 450 is seated into the recess 380 on the anchor body 110, and the detent 460 is seated into the recess 370 on the anchor body 110. As the detents 450/460 are seated into their respective recesses, they provide a tactile and/or audible feedback, for example a click that can be felt and/or heard by the healthcare professional as the detents fall into the mating recesses. The seated detents 450/460 inhibit the locking member 120 from rotating back into the locked position due to the physical contact between the side surfaces of the detents 450/460 and the side surfaces of the recesses 380/370. Of course, the locking is provisional in the sense that if a sufficient amount of force is applied to rotate the locking member 120, the locking member 120 can still overcome the physical obstruction caused by the detents 450/460, particularly as the detents 450/460 may be made of a resilient material. As such, the locking member 120 can still be rotated back into the locked position.

On the other hand, when the locking member 120 is rotated into the locked position (forming a tortuous path for the therapy delivery element 14 inside the open channel 150), the detents 450/460 protrude into the open channel 150. In other words, the detents 450/460 are surrounded on the sides by the side walls 250/260 of the anchor body 110. Therefore, further rotation of the locking member 120 is inhibited by the physical contact between the detents 450/460 and the sidewalls 250/260 of the channel 150. As such, the detents 450/460 provisionally lock the locking member 120 in the locked position. Again, if a sufficiently great force is applied to the locking member 120 to rotate it away from the locked position, the locking member 120 can still move away from the locked position. Of course, this is assuming that the suturing has not been done via the proximal suture loops yet. Once the proximal suture loops 310/340 have been sutured down, then the detents 450/460 help lock the locking member 120 in the locked position permanently.

As shown in FIGS. 11-14, the locking member 120 also includes a flange 452. Shaped similar to a "duckbill", the flange 452 is configured to come into physical contact with the protruding tab 350 of the anchor body 110 when the locking member 120 is rotated into the unlocked position. The physical contact maintains the locking member 120 at angle 475 with respect to axis 160 and prevents further rotation of the locking member 120 beyond the unlocked position and further away from the locked position. Without the flange 452 and/or the protruding tab 350, the locking member 120 may not necessarily stay at the unlocked position of angle 475 once it has been rotated there from the locked position. In other words, without anything stopping the rotation of the locking member 120, the locking member could have kept on rotating (e.g., due to inadvertent movement of the locking member) past the unlocked position at angle 475 such that the channel 150 and trough 400 would no longer be aligned. Here, the interaction between the flange 452 and the tab 350 stops the locking member 120 from further rotation away from the locked position once the locking member 120 reaches the unlocked position.

As discussed above, the detents 450/460 also prevents the rotation of the locking member 120 back toward the locked position. As such, both the detents 450/460 and the flange 452 and the protruding tab 350 facilitate the provisional locking of the locking member 120 in the unlocked position at angle 475 (see FIG. 21). It is understood that the "duckbill" profile of the flange 452 is merely a non-limiting example. The flange 452 may be configured to have other shapes or profiles in alternative embodiments as long as it can sufficiently engage with the protruding tab 350 to prevent the unintentional rotation of the locking member 120.

As shown in FIGS. 12-13 and 15, the unlocking member 120 also includes a recess (defined by its outer surface) 500. The recess 500 is shaped as a rectangle or a square in the illustrated embodiment, but it is understood that it may have other suitable shapes in alternative embodiments. The recess 500 is configured to receive a locking tool, for example a locking tool 510 illustrated in the side view of FIG. 16. In some embodiments, the locking tool 510 functions similar to a screwdriver. For example, it may have a tip having a shape that is configured to fit within, and occupy, the recess 500. As the body of the locking tool 510 is turned/rotated by the healthcare professional, the tip engages the side walls defining the recess 500, which causes the locking member 120 to rotate in the same direction as the locking tool 510.

Figure 16:
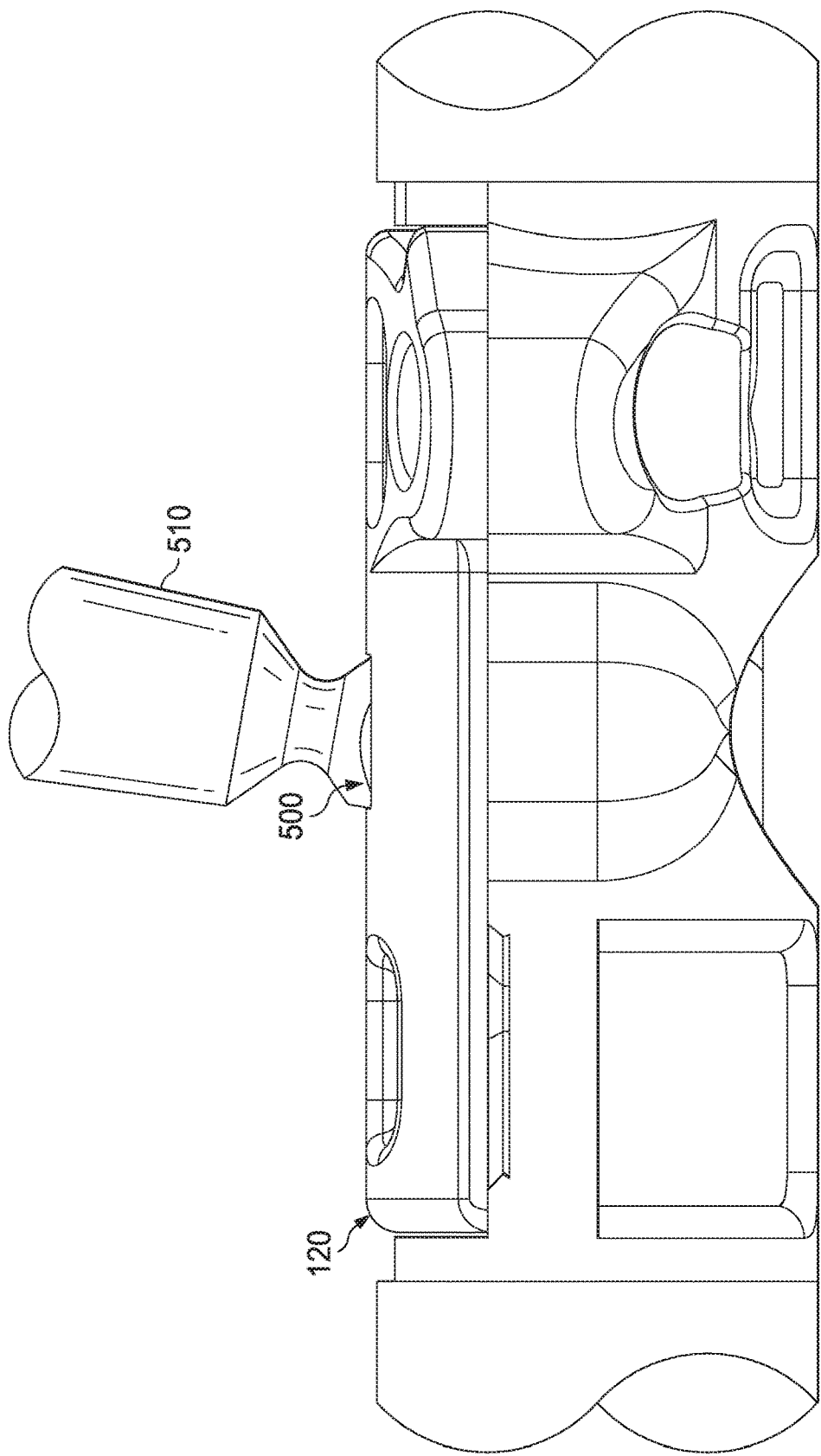
FIG. 16 is a side view of the anchoring device and a locking tool according to an embodiment of the present disclosure.

Using the locking tool 510, the healthcare professional may rotate the locking member 120 in a clockwise direction or in a counterclockwise direction. As such, the locking member 120 can be rotated between the unlocked position (with an open path for the therapy delivery element 14) and the locked position (with a tortuous path for the therapy delivery element 14). In some embodiments, the unlocked position and the locked position are separated by angle 475 of about 30 degrees (out of 360 degrees for a full circular rotation). Also as shown in FIG. 16, the locking tool 510 need not be inserted into the recess 500 in a perpendicular manner. Instead, the locking tool 510 can be inserted into the recess 500 at a non-right angle and still be capable of rotating the locking member 120. Furthermore, the recess 500 may be laser-marked to provide a clearer visual indication of the target for the locking tool. In some embodiments, the recess 500 may be made to be floorless, so that the therapy delivery element 14 will be more visible through the recess 500.

Referring now to FIGS. 7 and 17-19, the distal strain relief 130 and the proximal strain relief 140 are coupled to the distal ends and the proximal ends of the anchor body 110 and the locking member 120, respectively. The distal strain relief 130 and the proximal strain relief 140 are made of a pliable material. The distal strain relief 130 is longer than the proximal strain relief 140 in the illustrated embodiment, but this is not intended to be limiting.

According to embodiments of the present disclosure, the distal strain relief 130 includes an indicator for indicating a predefined distance. In the embodiment shown in FIG. 17, the indicator 550 is a longitudinal projection (e.g., shaped as a band or strip) that extends along the same axis 160 along which the open channel 150 extends. The indicator 550 is manufactured to have a predefined length 560, for example 1 centimeter in some embodiments. The predefined length 560 provides a visual reference for the healthcare professional during implantation and anchoring of the therapy delivery element 14.

Figure 18:
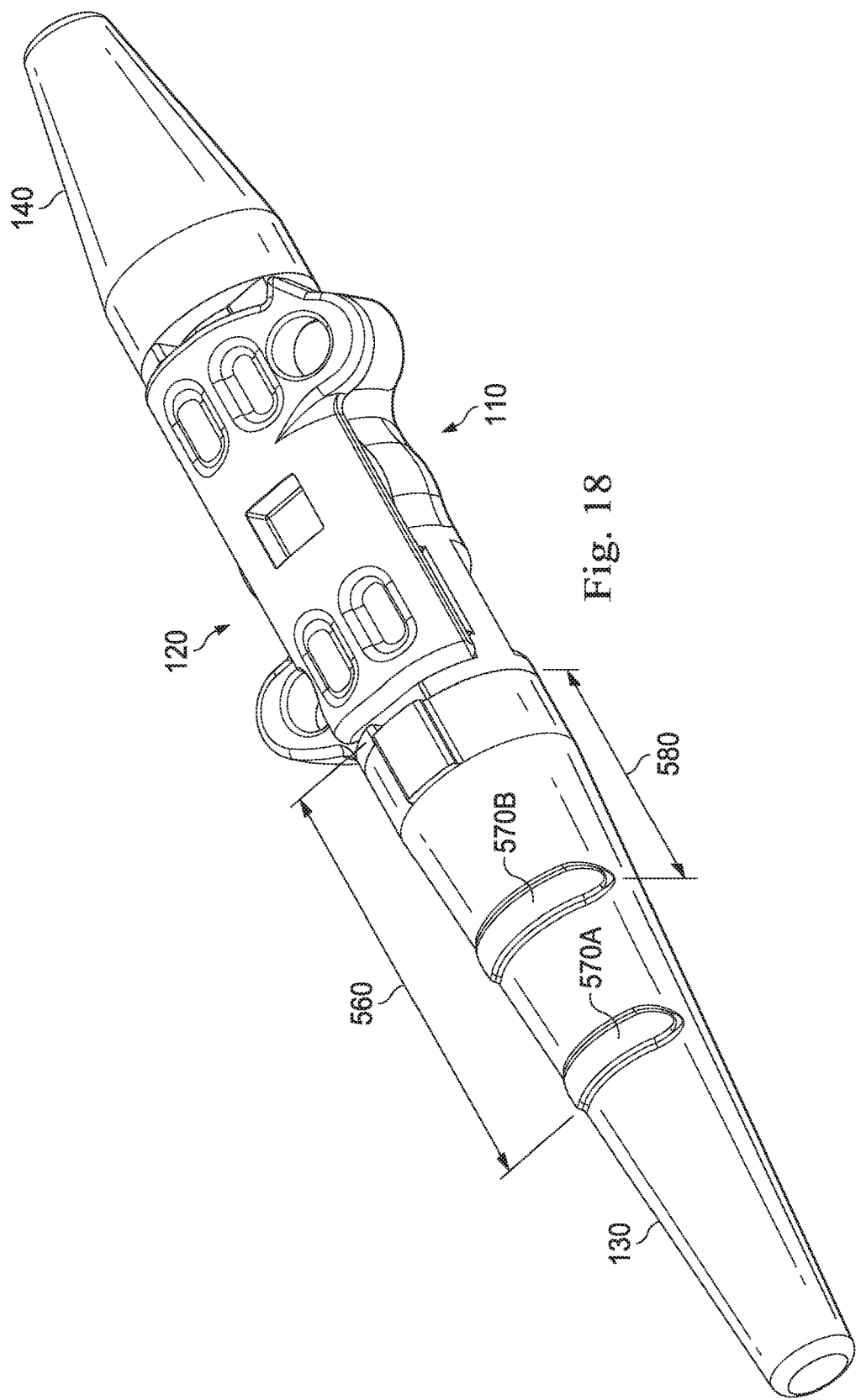
Figure 19:
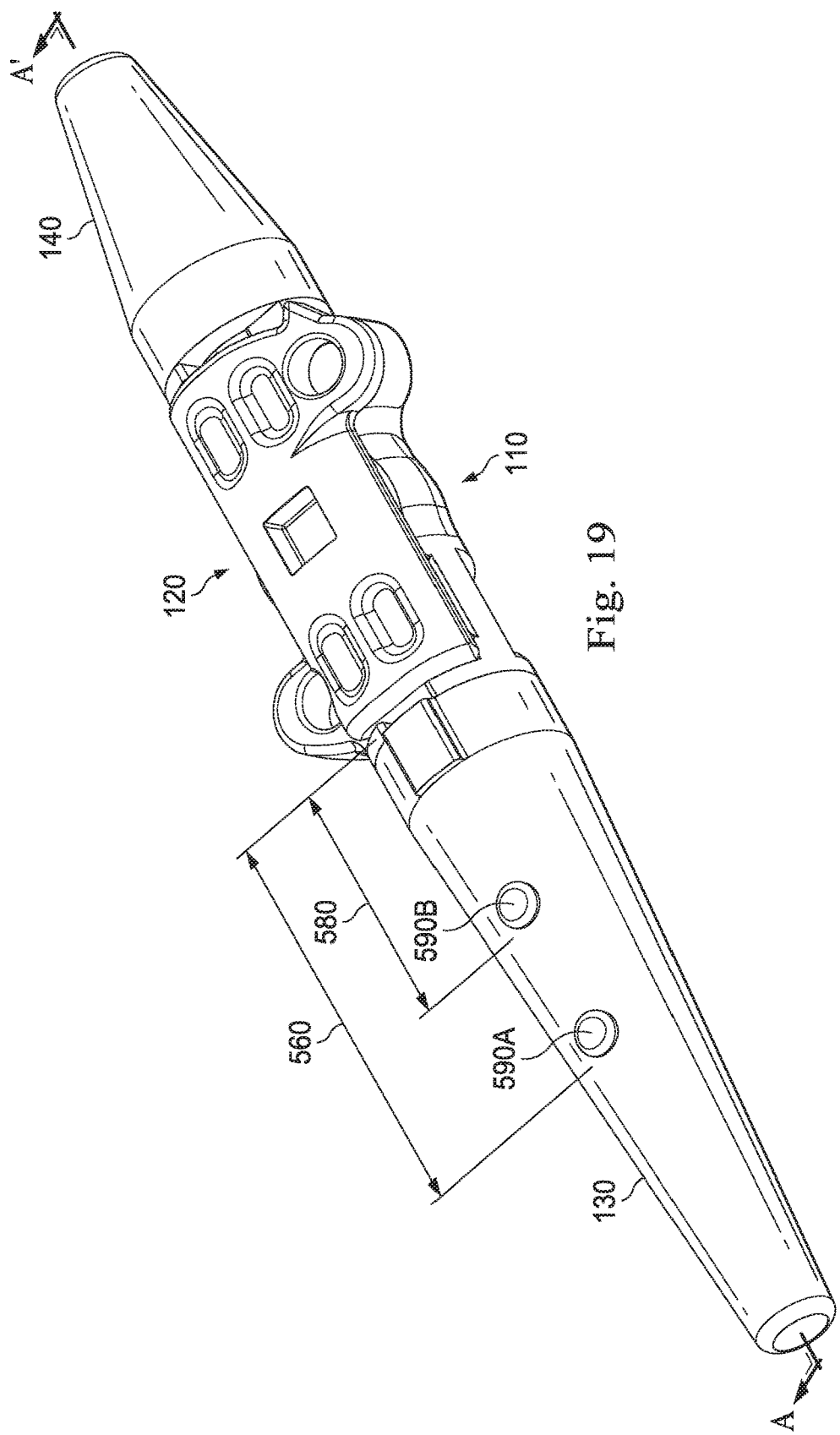

FIGS. 18-19 each illustrate an alternative embodiment of the indicator. In more detail, the indicator in FIG. 18 is in the form of two bars 570A and 570B. The bar 570A may be manufactured to have a distance 560 away from the end of distal strain relief 130 (or from the interface between the distal strain relief 130 and the unlocking member 120). For example, the distance 560 may be 1 centimeter. The bar 570B may be manufactured to have a distance 580 away from the end of distal strain relief 130. For example, the distance 580 may be 0.5 centimeters. In some embodiments, the bars 570A and 570B may also be manufactured to have a predefined distance separating themselves, for example 0.5 centimeters in some embodiments.

Similarly, the indicator in FIG. 19 is in the form of two dots 590A and 590B. The dot 590A may be manufactured to have a distance 560 away from the end of distal strain relief 130, and the dot 590B may be manufactured to have a distance 580 away from the end of distal strain relief 130. A predefined distance may also separate the two dots 590A/590B, similar to the bars 570A/570B in FIG. 18. Again, these predefined distances (e.g., distances 560 or 580) represented by the locations of the bars/dots 570A-B or 590A-B provide a visual reference guide for the healthcare professional.

FIG. 20A-20B illustrate diagrammatic perspective views of the anchoring device 100 according to another embodiment. The perspective view of FIG. 20A and the perspective view of FIG. 20B are taken from different angles. Similar to the embodiments shown in FIGS. 17-19, the embodiment of the anchoring device 100 shown in FIGS. 20A-20B also includes a position indicator 595 for indicating the predefined distance 560 discussed above. However, the position indicator 595 is a full radial protrusion around the distal strain relief 130 (circumferentially surrounding the distal strain relief 130). As such, one advantage provided by the embodiment in FIGS. 20A-20B is that it permits visual inspection of the position indicator 595 without requiring an alignment between the indicator and the channel. In the embodiments shown in FIGS. 17-19, the position indicators need to be at least partially aligned with the channel 150 to appear visible to a healthcare professional, since these position indicators only appear on a part (i.e., on one side) of the distal strain relief 130. In comparison, since the position indicator 595 in FIGS. 20A-20B protrudes circumferentially around the distal strain relief in 360 degrees, it remains visible to the healthcare professional from all angles.

Figure 17:
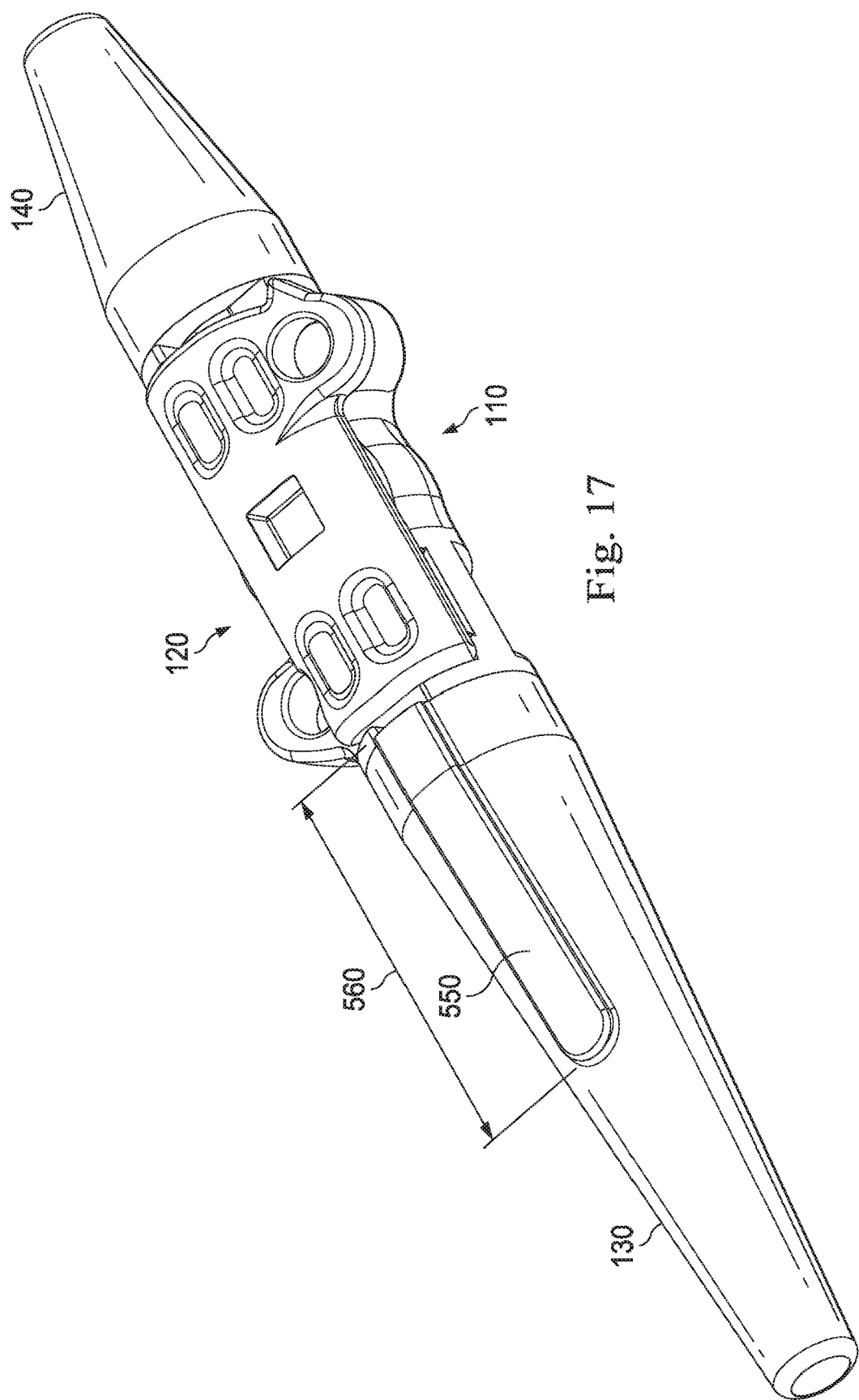

It is understood that the indicator is not limited to the specific examples illustrated in FIGS. 17-19. In other embodiments, the indicator may be in the form of other partial radial protrusions (where the bars 570A/570B may each be considered a specific embodiment of partial radial protrusion), other forms of full radial protrusions around the distal strain relief 130, or colored or uncolored bands (e.g., not protruding from the surface of the distal strain relief 130). It is also understood that an indicator similar to the indicator discussed herein may be implemented on the proximal strain relief 140 instead of, or in addition to, on the distal strain relief 130.

FIGS. 21-22 provide more cross-sectional view illustrations of the anchoring device 100 in the unlocked and locked configurations. In more detail, FIG. 21 illustrates a cross-sectional view of the anchoring device 100. The cross-sectional view is taken along line A/A' in FIG. 19, where the locking member 120 is partially blocked by the anchor body 110. The anchoring device 100 shown in FIG. 21 is also in the unlocked configuration, where the locking member 120 is rotated to the unlocked or open position. As discussed above with reference to FIG. 10, there is a window 280 defined by the opening 220 in the anchor body 110. The window 280 allows the healthcare professional to visually inspect a segment of the therapy delivery element 14 (not illustrated herein) located in the open channel. The open channel and the trough defined by the locking member 120 are aligned to form an open path where the therapy delivery element 14 can freely slide therethrough. The healthcare professional can see the movement of the therapy delivery element 14 via the window 280.

In comparison, FIG. 22 illustrates a cross-sectional view of the anchoring device 100 similar to that of FIG. 21, except that the anchoring device 100 is now in the locked configuration. The locking member 120 is rotated to the locked position and is blocked in its substantial entirety by the anchor body 110. The open channel and the trough defined by the locking member 120 are misaligned by an angle 475 to define a tortuous path to restrict the movement of the therapy delivery element 14 (not illustrated herein). This causes a segment of the therapy delivery element 14 to be "pinched" and therefore locked within the open channel. The pinched position of the therapy delivery element 14 is also viewable to the healthcare professional through the window 280. In addition, FIG. 22 also illustrates the detents 450/460 being seated in the recess defined by the open channel 150. Again, the detents facilitate a provisional locking of the anchoring device 100 in the locked configuration.

FIGS. 23-24 illustrate cross-sectional views of the anchoring device 100 with the therapy delivery element 14 positioned therein. In more detail, FIG. 23 shows the therapy delivery element 14 located in the anchoring device 100 when the anchoring device is in the open position, such that the therapy delivery element 14 can be moved freely along the open channel 150 as discussed above. In comparison, FIG. 24 shows the therapy delivery element 14 located in the anchoring device 100 when the anchoring device is in the closed or locked position, such that the movement of the therapy delivery element 14 along the channel 150 is inhibited as discussed above.

Figure 25:
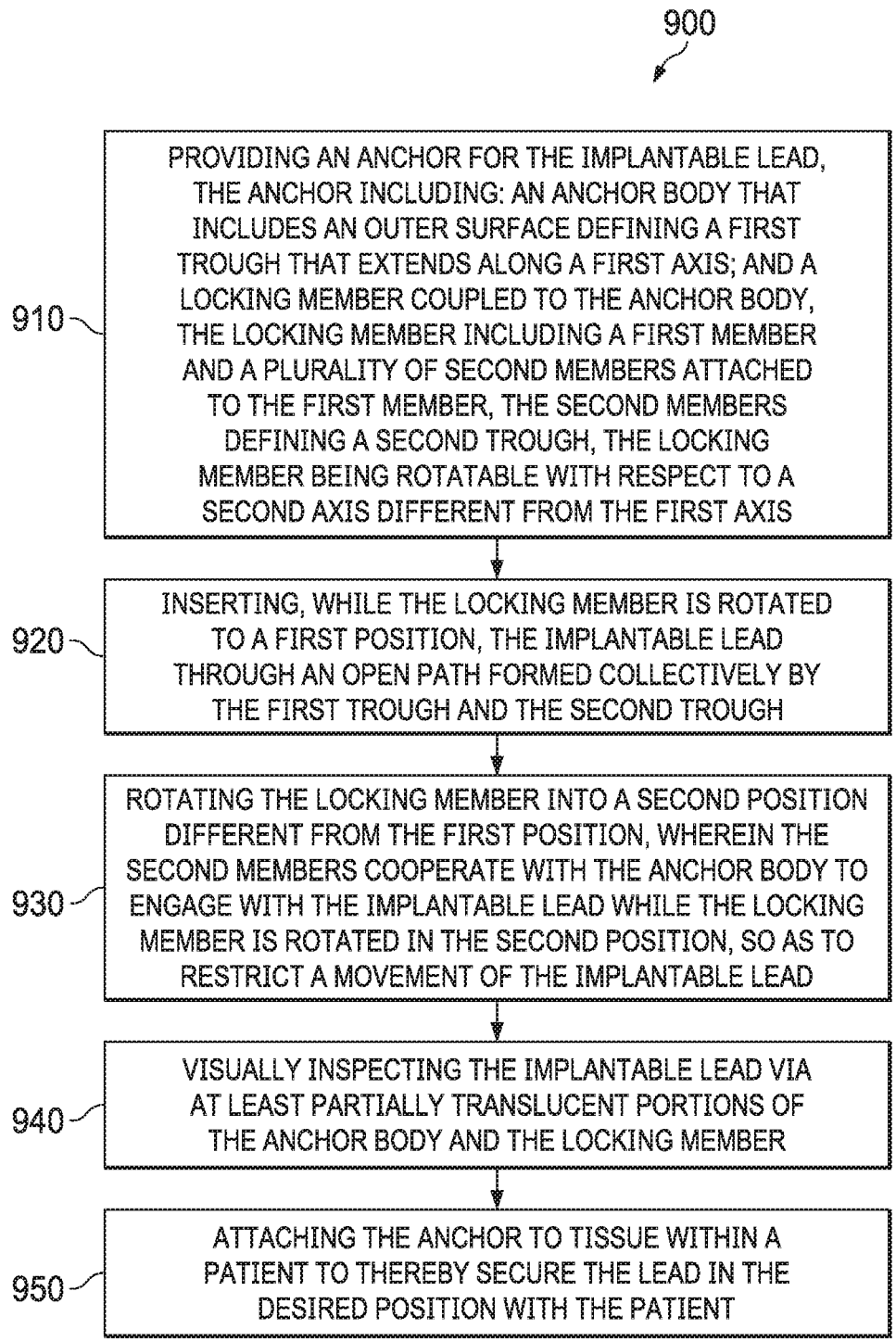
FIG. 25 is an example flowchart illustrating a method of implanting a medical device according to various aspects of the present disclosure.

FIG. 25 is a flowchart illustrating a method 900 of anchoring an implantable lead that is configured to deliver electrical stimulation for a patient. In some embodiments, the steps of the method 900 are performed by a healthcare professional, such as a surgeon.

The method 900 includes a step 910 of providing an anchor for the implantable lead inside the patient. The anchor includes an anchor body that includes an outer surface defining a first trough that extends along a first axis. The anchor also includes a locking member coupled to the anchor body. The locking member includes a first member and a plurality of second members attached to the first member. The second members define a second trough. The locking member is rotatable with respect to a second axis different from the first axis. For example, the second axis may be perpendicular to the first axis. In some embodiments, the anchor further comprises: a proximal strain relief coupled to a proximal end of the anchor body; and a distal strain relief coupled to a distal end of the anchor body, wherein the distal strain relief includes an indicator for indicating a predefined distance. In some embodiments, the indicator is selected from the group consisting of: a longitudinal projection, a radial protrusion, and one or more bands. In some embodiments, the U-shaped cross-sectional profile of the first trough is defined by a first side wall, a second side wall, and a floor joining the first side wall and the second side wall, of the out surface.

The method 900 includes a step 920 of inserting the implantable lead through an open path formed collectively by the first trough and the second trough. The step 920 is performed while the locking member is rotated to a first position. In some embodiments, the first trough has a U-shaped cross-sectional profile oriented in a first direction, and the second trough has U-shaped cross-sectional profile oriented in a second direction opposite the first direction.

The method 900 includes a step 930 of rotating the locking member into a second position different from the first position. The second members cooperate with the anchor body to engage with the implantable lead while the locking member is rotated in the second position, so as to restrict a movement of the implantable lead. In some embodiments, the rotating comprises: inserting a locking tool into a recess of the locking member; and rotating the locking tool. In some embodiments, the inserting the locking tool is performed such that the locking tool is inserted into the recess at a non-right angle. In some embodiments, the second members each have a blunted corner configured to engage the implantable lead, the blunted corner having a radius in a range between 0.004 inches and 0.006 inches.

The method 900 includes a step 940 of visually inspecting the implantable lead via at least partially translucent portions of the anchor body and the locking member.

The method includes a step 950 of attaching the anchor to tissue within a patient to thereby secure the lead in the desired position with the patient.

It is understood that some of the steps 910/940 need not necessarily be performed sequentially unless otherwise specified. It is also understood that the method 910/940 may include additional steps that may be performed before, during, or after the steps 910/940. For example, the method 900 may include the following steps: suturing the anchor body to a tissue of the patient via a distal suture loop located on the anchor body; moving, after the anchor body has been sutured, the implantable lead through the open path while the locking member is rotated to the first position; rotating the locking member to the second position, wherein a first proximal suture loop located on the anchor body is aligned with a second proximal suture loop located on the locking member; and suturing the anchor body and the locking member to the tissue after the first proximal suture loop and the second proximal suture loop are aligned. As another example, the method 900 may include a step of provisionally locking the locking member in the first position by protruding a detent of the first member into a recess located on the anchor body, so as to prevent unintended rotation of the locking member back into the second position. As yet another example, the method 900 may include a step of preventing a further rotation of the locking member beyond the first position and away from the second position by creating a physical contact between a protruding tab of the anchor body and a flange of the locking member when the locking member is rotated into the first position.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A device for anchoring an implantable medical device inside a body, the device comprising:
   an anchor body that includes an outer surface defining a first trough that extends along a first axis, the first trough being configured to receive a portion of the implantable medical device, wherein the first trough includes a cavity; and
   a locking member coupled to the anchor body and configured to rotate with respect to a second axis different from the first axis, so that the locking member is rotatable between a first position and a second position;
   wherein:

the first trough has a U-shaped cross-sectional profile oriented in a first direction, the U-shaped cross-sectional profile being defined by a first side wall, a second side wall parallel to the first side wall, and a floor joining the first side wall and the second side wall, of the outer surface;

the locking member includes a first member and a plurality of second members attached to the first member, the second members protruding outwardly from the first member and insert-able into the cavity to couple the locking member to the anchor body;

the first member is configured to provide a cover for at least a portion of the first trough when the locking member is rotated to the second position;

the second members define a second trough that is aligned with the first trough when the second members are inserted into the cavity and the locking member is rotated to the first position, so as to form an open path for the implantable medical device to move through the first and second troughs;

the locking member extends in a third axis that is aligned with the first axis when the locking member is rotated to the second position;

the second trough extends in a fourth axis different from, but not perpendicular to, the third axis; and the second members block at least a portion of the first trough to define a tortuous path between the first trough and the second trough when the locking member is rotated to the second position, so as to restrict a movement of the implantable medical device through the first and second troughs.

2. The device of claim 1, wherein the second trough has U-shaped cross-sectional profile oriented in a second direction opposite the first direction.

3. The device of claim 2, wherein the floor has a curved cross-sectional profile.

4. The device of claim 1, wherein the second members are configured to pinch the implantable medical device against the first trough when the locking member is rotated to the second position.

5. The device of claim 1, wherein the second members each have a blunted corner configured to engage the implantable medical device, and wherein the implantable medical device includes an elongated lead having electrodes for delivering electrical stimulation.

6. The device of claim 5, wherein the blunted corner has a radius in a range between 0.004 inches and 0.006 inches.

7. The device of claim 1, wherein:
the anchor body includes a recess;
the first member of the locking member includes a detent; and
when the locking member is rotated into the first position, the detent provisionally locks the locking member in the first position by protruding into the recess, so as to prevent inadvertent rotation of the locking member back into the second position.

8. The device of claim 7, wherein the detent is configured to provide an audible and tactile feedback to a user in response to the locking member being provisionally locked in the first position.

9. The device of claim 1, wherein the second axis is perpendicular to the first axis, and wherein an intersection between the first axis and the second axis defines an angle that is in a range between about 20 degrees and about 40 degrees.

10. The device of claim 1, wherein:
the anchor body includes a protruding tab; and
the locking member includes a flange that is configured to come into physical contact with the protruding tab when the locking member is rotated into the first position, thereby preventing further rotation of the locking member beyond the first position and away from the second position.

11. The device of claim 1, wherein at least portions of the anchor body and the locking member are sufficiently translucent to allow for visual inspection of the implantable medical device received therein.

12. The device of claim 1, wherein:
the anchor body includes a distal suture loop and a first proximal suture loop, the locking member being movably independent from the distal suture loop; and
the locking member includes a second proximal suture loop that is aligned with the first proximal suture loop when the locking member is rotated into the second position.

13. The device of claim 1, wherein the locking member contains a recess that is configured to receive a locking tool for rotating the locking member into the first position or the second position.

14. The device of claim 1, further comprising:
a proximal strain relief coupled to a proximal end of the anchor body; and
a distal strain relief coupled to a distal end of the anchor body, wherein the distal strain relief includes an indicator for indicating a predefined distance.

15. The device of claim 14, wherein the indicator is selected from the group consisting of: a longitudinal projection, a radial protrusion, and one or more bands.

16. The device of claim 1, wherein a segment of the implantable medical device in the second trough is visible through an at least partially transparent window in the anchor body.

17. A device for anchoring an implantable medical device inside a body, the device comprising:
an anchor body that includes an exterior surface defining an open channel that extends along a first axis, the open channel being outwardly open through an entirety of the first axis of the anchor body and is configured to receive a portion of the implantable medical device; and
a locking member coupled to the anchor body and configured to rotate between a first position and a second position with respect to a second axis different from the first axis, so that:
in an unlocked configuration corresponding to the first position, the locking member cooperates with the anchor body to define an open path for the implantable medical device to move therethrough; and
in a locked configuration corresponding to the second position, the locking member cooperates with the anchor body to restrict movement of the implantable medical device;
wherein:
the locking member includes a detent that provisionally locks the locking member in the second position by protruding into the open channel so that a sidewall of the detent is in physical contact with sidewalls of the open channel, thereby inhibiting further rotation of the locking member with respect to the anchor body beyond the second position; and
the anchor body includes recesses for seating the detent when the locking member is rotated into the first position, the seated detent provisionally locking the locking member in the first position.

18. The device of claim 17, wherein:
the anchor body includes a protruding tab; and
the locking member includes a projection that is configured to come into physical contact with the protruding tab when the locking member is rotated into the first position, thereby preventing further rotation of the locking member beyond the first position and away from the second position.

19. The device of claim 17, wherein:
the open channel includes a cavity;
the locking member includes a first member and a plurality of second members attached to the first member, the second members protruding outwardly from the first member and insert-able into the cavity;
the second members define a trench that is aligned with the open channel when the second members are inserted into the cavity and the locking member is rotated to the first position, so as to form an open path for the implantable medical device to move therethrough; and
the second members define a tortuous path between the open channel and the trench when the locking member is rotated to the second position, so as to restrict a movement of the implantable medical device.

20. The device of claim 19, wherein a segment of the implantable medical device is visible through a window in the anchor body that is at least partially transparent, and wherein the implantable medical device includes an elongated lead having electrodes for delivering electrical stimulation.

21. The device of claim 17, wherein the open channel has a U-shaped cross-sectional profile oriented in a first direction, and the locking member defines a recess that has a U-shaped cross-sectional profile oriented in a second direction opposite the first direction.

22. The device of claim 21, wherein the U-shaped cross-sectional profile of the open channel is defined by a first side wall, a second side wall, and a floor joining the first side wall and the second side wall, of the outer surface.

23. The device of claim 17, wherein the locking member has protruding members that cooperate with the anchor body to restrict the movement of the implantable medical device, the protruding members each having a blunted corner configured to engage the implantable medical device, the blunted corner having a radius in a range between 0.004 inches and 0.006 inches.

24. The device of claim 17, wherein:
the second axis is perpendicular to the first axis;
the locking member extends in a third axis that is aligned with the first axis when the locking member is rotated to the second position; and
the locking member defines a trough that extends in a fourth axis different from, but not perpendicular to, the third axis.

25. The device of claim 17, wherein at least portions of the anchor body and the locking member are sufficiently translucent to allow for visual inspection of the implantable medical device received therein.

26. The device of claim 17, wherein:
the anchor body includes a distal suture loop and a first proximal suture loop, the locking member being movably independent from the distal suture loop; and
the locking member includes a second proximal suture loop that is aligned with the first proximal suture loop when the locking member is rotated into the second position.

27. The device of claim 17, wherein the locking member contains a recess that is configured to receive a locking tool for rotating the locking member into the first position or the second position.

28. The device of claim 17, further comprising:
a proximal strain relief coupled to a proximal end of the anchor body; and
a distal strain relief coupled to a distal end of the anchor body, wherein the distal strain relief includes an indicator for indicating a predefined distance.

29. The device of claim 28, wherein the indicator is selected from the group consisting of: a longitudinal projection, a radial protrusion, and one or more bands.

30. A device for anchoring an implantable medical device inside a body, the device comprising:
an anchor body that includes an outer surface defining a first trough that extends along a first axis, the first trough being configured to receive a portion of the implantable medical device, wherein the first trough includes a cavity; and
a locking member coupled to the anchor body and configured to rotate with respect to a second axis different from the first axis, so that the locking member is rotatable between a first position and a second position;
wherein:
the locking member includes a first member and a plurality of second members attached to the first member, the second members protruding outwardly from the first member and insert-able into the cavity;
the first member is configured to provide a cover for at least a portion of the first trough when the locking member is rotated to the second position;
the second members define a second trough that is aligned with the first trough when the second members are inserted into the cavity and the locking member is rotated to the first position, so as to form an open path for the implantable medical device to move through the first and second troughs;
the second members have at least one corner configured to engage the implantable medical device when the locking member is rotated to the second position, so as to restrict a movement of the implantable medical device without damaging the implantable medical device, the corner having a radius between 0.002 inches and 0.010 inches;
the anchor body includes a recess;
the first member of the locking member includes a detent that protrudes outwardly in a same direction as the second members;
when the locking member is rotated into the first position, the detent provisionally locks the locking member in the first position by protruding into the recess, so as to prevent inadvertent rotation of the locking member back into the second position; and
when the locking member is rotated into the second position, a sidewall of the detent is in physical contact with a sidewall of the first trough, thereby inhibiting further rotation of the locking member with respect to the anchor body.

31. The device of claim 30, wherein:
the second trough extends along a third axis different from the first axis when the locking member is rotated to the second position;
the first axis and the third axis are on a same lateral plane; and
the second axis is orthogonal to the lateral plane.

32. The device of claim 30, wherein the radius is in a range between 0.004 inches and 0.008 inches, and wherein the implantable medical device includes an elongated lead having electrodes for delivering electrical stimulation.

33. The device of claim 30, wherein the first trough has a U-shaped cross-sectional profile oriented in a first direction, and the second trough has U-shaped cross-sectional profile oriented in a second direction opposite the first direction.

34. The device of claim 33, wherein the U-shaped cross-sectional profile of the first trough is defined by a first side wall, a second side wall, and a floor joining the first side wall and the second side wall, of the outer surface.

35. The device of claim 30, wherein the second members are configured to pinch the implantable medical device against the first trough when the locking member is rotated to the second position.

36. The device of claim 34, wherein: the first side wall is parallel to the second side wall.

37. The device of claim 36, wherein the detent is configured to provide an audible and tactile feedback to a user in response to the locking member being provisionally locked in the first position.

38. The device of claim 30, wherein the second axis is perpendicular to the first axis.

39. The device of claim 30, wherein:
the anchor body includes a protruding tab; and
the locking member includes a flange that is configured to come into physical contact with the protruding tab when the locking member is rotated into the first position, thereby preventing further rotation of the locking member beyond the first position and away from the second position.

40. The device of claim 30, wherein at least portions of the anchor body and the locking member are sufficiently translucent to allow for visual inspection of the implantable medical device received therein.

41. The device of claim 30, wherein:
the anchor body includes a distal suture loop and a first proximal suture loop, the locking member being movably independent from the distal suture loop; and
the locking member includes a second proximal suture loop that is aligned with the first proximal suture loop when the locking member is rotated into the second position.

42. The device of claim 30, wherein the locking member contains a recess that is configured to receive a locking tool for rotating the locking member into the first position or the second position.

43. The device of claim 30, further comprising:
a proximal strain relief coupled to a proximal end of the anchor body; and
a distal strain relief coupled to a distal end of the anchor body, wherein the distal strain relief includes an indicator for indicating a predefined distance.

44. The device of claim 43, wherein the indicator is selected from the group consisting of: a longitudinal projection, a radial protrusion, and one or more bands.

45. The device of claim 30, wherein a segment of the implantable medical device in the second trough is visible through a window in the anchor body, the window being at least partially transparent.

46. A method of anchoring an implantable medical device inside a patient, comprising:
providing an anchor for the implantable medical device, the anchor including:
an anchor body that includes an outer surface defining a first trough that extends along a first axis and having U-shaped cross-sectional profile oriented in a first direction, wherein the U-shaped cross-sectional profile of the first trough is defined by a first side wall, a second side wall parallel to the first side wall, and a floor joining the first side wall and the second side wall, of the outer surface; and
a locking member coupled to the anchor body, the locking member including a first member and a plurality of second members attached to the first member, the second members defining a second trough, the locking member being rotatable with respect to a second axis different from the first axis;
inserting, while the locking member is rotated to a first position, the implantable medical device through an open path formed collectively by the first trough and the second trough;
rotating the locking member into a second position different from the first position, wherein the second members cooperate with the anchor body to engage with the implantable medical device while the locking member is rotated in the second position, so as to restrict a movement of the implantable medical device, wherein when the locking member is rotated into the second position, a detent of the first member protrudes into the first trough, thereby inhibiting further rotation of the locking member with respect to the anchor body; and
attaching the anchor to tissue within a patent to thereby anchor the location of the implantable medical device.

47. The method of claim 46, further comprising:
suturing the anchor body to a tissue of the patient via a distal suture loop located on the anchor body;
moving, after the anchor body has been sutured, the implantable medical device through the open path while the locking member is rotated to the first position;
rotating the locking member to the second position, wherein a first proximal suture loop located on the anchor body is aligned with a second proximal suture loop located on the locking member; and
suturing the anchor body and the locking member to the tissue after the first proximal suture loop and the second proximal suture loop are aligned.

48. The method of claim 46, further comprising: provisionally locking the locking member in the first position by protruding the detent of the first member into a recess located on the anchor body, so as to prevent unintended rotation of the locking member back into the second position.

49. The method of claim 46, further comprising: preventing a further rotation of the locking member beyond the first position and away from the second position by creating a physical contact between a protruding tab of the anchor body and a flange of the locking member when the locking member is rotated into the first position.

50. The method of claim 46, further comprising: visually inspecting the implantable medical device via at least partially translucent portions of the anchor body and the locking member.

51. The method of claim 46, wherein the rotating comprises:
inserting a locking tool into a recess of the locking member; and
rotating the locking tool.

52. The method of claim 51, wherein the inserting of the locking tool is performed so that the locking tool is inserted into the recess at a non-right angle.

53. The method of claim 46, wherein the anchor further comprises:
- a proximal strain relief coupled to a proximal end of the anchor body; and
- a distal strain relief coupled to a distal end of the anchor body, wherein the distal strain relief includes an indicator for indicating a predefined distance.

54. The method of claim 53, wherein the indicator is selected from the group consisting of: a longitudinal projection, a radial protrusion, and one or more bands.

55. The method of claim 46, wherein the second axis is perpendicular to the first axis.

56. The method of claim 46, wherein the second trough has U-shaped cross-sectional profile oriented in a second direction opposite the first direction.

57. The method of claim 56, wherein the floor has a curved cross-sectional profile.

58. The method of claim 46, wherein the second members each have a blunted corner configured to engage the implantable medical device, the blunted corner having a radius in a range between 0.004 inch and 0.006 inch.

* * * * *